(12) United States Patent
Dibrov et al.

(10) Patent No.: US 10,744,111 B2
(45) Date of Patent: *Aug. 18, 2020

(54) DERIVATIVES OF KORORMICIN USEFUL AS ANTIBIOTICS

(71) Applicants: Pavel Dibrov, Winnipeg (CA); Elena Dibrov, Winnipeg (CA); Grant Pierce, Winnipeg (CA)

(72) Inventors: Pavel Dibrov, Winnipeg (CA); Elena Dibrov, Winnipeg (CA); Grant Pierce, Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,117

(22) Filed: Nov. 15, 2018

(65) Prior Publication Data

US 2019/0083450 A1 Mar. 21, 2019

Related U.S. Application Data

(63) Continuation of application No. 15/500,006, filed as application No. PCT/CA2016/050470 on Apr. 22, 2016, now Pat. No. 10,166,213.

(Continued)

(51) Int. Cl.
*A61K 31/341* (2006.01)
*C07D 307/66* (2006.01)
(Continued)

(52) U.S. Cl.
CPC ............ *A61K 31/341* (2013.01); *A61K 31/16* (2013.01); *A61K 31/365* (2013.01); *A61P 31/04* (2018.01);
(Continued)

(58) Field of Classification Search
CPC .. A61K 2300/00; A61K 31/16; A61K 31/341; A61K 31/365; A61P 31/04;
(Continued)

(56) References Cited

U.S. PATENT DOCUMENTS 10,166,213 B2 * 1/2019 Dibrov ............... C07D 307/66

FOREIGN PATENT DOCUMENTS

JP 2000-281670 10/2000
JP 2000-336088 12/2000
(Continued)

OTHER PUBLICATIONS

Tebben et al. (Mar. Drugs 2014, 12; 2802-2815).*
(Continued)

*Primary Examiner* — Valerie Rodriguez-Garcia
(74) *Attorney, Agent, or Firm* — Knobbe, Martens, Olson & Bear, LLP

(57) ABSTRACT

An antibiotic compound of formula (III):

or a salt or stereoisomer thereof; wherein $R^1$-$R^3$ and $R^5$-$R^{10}$ are independently selected from the group consisting of H, alkyl group, substituted alkyl group, halogen, OH, $NH_2$ and SH; $R^4$ is H, alkyl group or substituted alkyl group; $X^1$-$X^2$ are independently selected from the group consisting of =O, =S, NH, H, alkyl, halogen, OH, SH and $NH_2$; W is a saturated acyclic hydrocarbon chain of 1 to 15 carbon atoms; and Z is a neutral or positively charged organic group. The compounds are useful in treating bacterial diseases.

21 Claims, 25 Drawing Sheets

Related U.S. Application Data

(60) Provisional application No. 62/151,902, filed on Apr. 23, 2015.

(51) Int. Cl.
| | | |
|---|---|---|
| *C07F 9/655* | (2006.01) | |
| *A61P 31/04* | (2006.01) | |
| *A61K 31/16* | (2006.01) | |
| *A61K 31/365* | (2006.01) | |
| *C07D 309/30* | (2006.01) | |

(52) U.S. Cl.
CPC ......... *C07D 307/66* (2013.01); *C07D 309/30* (2013.01); *C07F 9/655* (2013.01); *C07F 9/65515* (2013.01); *A61K 2300/00* (2013.01); *Y02A 50/406* (2018.01); *Y02A 50/478* (2018.01); *Y02A 50/483* (2018.01)

(58) Field of Classification Search
CPC ..... C07D 307/66; C07D 309/30; C07F 9/655; C07F 9/65515; Y02A 50/406; Y02A 50/478; Y02A 50/483
See application file for complete search history.

(56) References Cited

FOREIGN PATENT DOCUMENTS

| JP | 2001-010908 | 1/2001 |
|---|---|---|
| JP | 2003-061645 | 3/2003 |
| JP | 3905604 | 4/2007 |

OTHER PUBLICATIONS

Dibrov, P. et al. 2017 "Development of a novel rationally designed antibiotic to inhibit a nontraditional bacterial target" *Can J Physiol Pharmacol* 95: 595-603.

Ito, T. et al. 2017 "Identification of the binding sites for ubiquinone and inhibitors in the $Na^+$-pumping NADH-ubiquinone oxidoreductase from *Vibro cholera* by photoaffinity labeling" *J Biol Chem* 292(19): 7727-7742.

Supplementary European Search Report in corresponding European Application No. EP 16 78 2435, dated Jan. 8, 2019.

Hase, et al., 2001 "Sodium ion cycle in bacterial pathogens: evidence from cross-genome comparisons", *Microbiology and Molecular Biology Reviews* 65(3): 353-370.

Hayashi, et al., 2001 "Recent progress in the Na+-translocating NADH-quinone reductase from the marine Vibrio alginolyticus" *Biochimica et Biophysica Acta*, 1505: 37-44.

Hayashi, et al., 2002 "Korormicin insensitivity in *Vibrio alginolyticus* is correlated with a single point mutation of Gly-140 in the NqrB subunit of the Na+-translocating NADH-quinone reductase", *Archives of Biochemistry and Biophysics*, 401(2): 173-177.

Johansen, et al., 2008 "On a fishing expedition for new bioactive and antibacterial substances—a report from the ocean", *HCAPLUS* 89(11): 12-17.

Kobayashi, 1999 "Development of highly reactive reagents for the coupling reactions and application to syntheses of prostaglandins and leukotrienes", *Recent Research Developments in Organic Chemistry* 3(Pt. 1): 61-77.

Kobayashi, et al., 2000 "Determination of the stereoisomer of korormicin from eight possible stereoisomers by total synthesis", *Tetrahedron Letters* 41(9): 1465-1468.

Kobayashi, et al. 2001 "Total Synthesis of Korormicin" *European Journal of Organic Chemistry*: 1873-1881.

Nakayama, et al., 1999 "Inhibitor studies of a new antibiotic, Korormicin, 2-n-heptyl-4-hydroxyquinoline N-oxide and Ag+ toward the Na+-translocating NADH-quinone reductase from the marine *Vibrio alginolyticus*", *Biological & Pharmaceutical Bulletin* 22(10): 1064-1067.

Sting, et al., 2001 "(R,R)-2-t-Butyl-5-methyl-1,3-dioxolan-4-one", *e-EROS Encyclopedia of Reagents for Organic Synthesis* in 5 pages.

Tebben, et al. 2014 "A coralline algal-associated bacterium, *Pseudoalteromonas* strain J010, yields give new korormicins and a bromopyrrole" *Marine Drugs* 12: 2802-2815.

Uehara, et al., 1999 "The absolute configuration and total synthesis of korormicin", *Tetrahedron Letters* 40(49): 8641-8645.

Yoshikawa, et al. 1997 "Korormicin, a novel antibiotic specifically active against marine gram-negative bacteria, produced by a marine bacterium" *The Journal of Antibiotics* 50(11): 949-953.

Yoshikawa, et al., 1999 "Korormicin, an antibiotic specific for gram-negative marine bacteria, strongly inhibits the respiratory chain-linked Na+-translocating NADH: quinone reductase from the marine *Vibrio alginolyticus*", *Journal of Antibiotics* 52(2): 182-185.

Yoshikawa, et al. 2003 "Planar structure and antibacterial activity of korormicin derivatives isolated from *Pseudoalteromonas* sp. F-420" *The Journal of Antibiotics* 56(10): 866-870.

\* cited by examiner

HQNO (5S,3'R,9'S,10'R)-1

PEG-2

FIGURE 9

After single application of PEG-2 C. trachomatis inclusions are small and hollow control infection            20 µM I PEG-2

- HELA cells were infected with C. trachomatis ($10^3$ IFU per $10^5$ cells)
- PEG-2 was added with DMEM (2 hours after initial attachment of Ctr)

N-decanoyl-L-Homoserine lactone

N-butyryl-L-Homoserine lactone

N-3-oxo-dodecanoyl-L-Homoserine lactone

N-hexanoyl-L-Homoserine lactone

FIGURE 24

Treatment with derivatives of PEG-2 reduces size of
*Chlamydia trachomatis* inclusions in infected cells

*Chlamydia trachomatis* infection, no treatment

PEG-2S, 1μM

PEG-6(BOC), μM

PEG-10, 1μM

PEG-11, 1μM

PEG-14, 1μM

DERIVATIVES OF KORORMICIN USEFUL AS ANTIBIOTICS

RELATED APPLICATIONS

This application is a continuation of U.S. application Ser. No. 15/500,006, filed Jan. 27, 2017, which is the U.S. national phase of International Application No. PCT/CA2016/050470, filed Apr. 22, 2016, which claims benefit of U.S. Provisional Application No. 62/151,902, filed Apr. 23, 2015, all of which are expressly incorporated by reference in their entireties.

BACKGROUND OF THE INVENTION

Field of the Invention

The present invention relates to antibiotic compounds and therapeutic uses thereof.

Description of the Related Art

A global crisis regarding treatment and control of bacterial infections is well recognized. Medical concerns include a lack of sufficient variety of antibiotics to address new infections emerging in the world and resistance to conventional antibiotic treatment that has been observed in adapting bacteria. New antibiotics to address the situation have not been created. In the mid-1980's 16 new antibiotics were approved by the FDA. In 2008/09, this had decreased to just one (Infectious Diseases Society of America). During the same approximate time period, resistance to antibiotics had climbed from an incidence of ~5% to 30-60%. This has prompted the World Health Organization to state in 2009 that the "rapid development of anti-microbial resistance is one of the three greatest threats to human health."

Part of the problem in identifying new drugs to address this crisis is that industry has depleted itself of targets to control bacteria. The targets that have been conventionally used in the past and are common for all bacteria today include prokaryotic ribosomes, enzymes working on DNA & RNA, and the synthesis of cell walls, etc. Virtually no new mechanistic targets have been identified.

The $Na^+$-translocating NADH: ubiquinone oxidoreductase ($Na^+$-NQR) in bacteria has been suggested as a mechanism to control bacterial replication and viability. Three inhibitors of $Na^+$-NQR have been reported so far: denaturing $Ag^+$ ions, (3R,4Z,6E)-N-[(5S)-5-Ethyl-5-methyl-2-oxo-2,5-dihydro-3-furanyl]-3-hydroxy-8-[(2 S,3R)-3-octyl-2-oxiranyl]-4,6-octadienamide (korormicin), and 2-n-heptyl-4-hydroxyquinoline N-oxide (HQNO). $Ag^+$ ions have obvious delivery problems and are non-specific as well. Both korormicin and HQNO have been shown to inhibit the sodium-dependent ubiquinone reduction by $Na^+$-NQR in a mutually exclusive manner and both have been suggested to possess antimicrobial activity (as discussed for example, in Japanese Patent 3905604B2 published 18 Apr. 2007, Japanese Patent Application Publication 2000336088 published 5 Dec. 2000, and Japanese Patent Application Publication 2001010908 published 16 Jan. 2001). However, none of these compounds have been developed as an effective antibiotic treatment for animals, for example mammals, or more particularly humans.

Accordingly, there is a continuing need for alternative antibiotic compounds.

SUMMARY OF THE INVENTION

In an aspect there is provided, an antibiotic compound of formula (III):

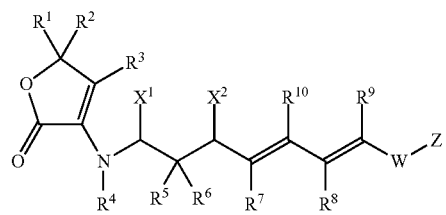

or a salt or stereoisomer thereof;
wherein $R^1$-$R^3$ and $R^5$-$R^{10}$ are independently selected from H, alkyl group, substituted alkyl group, halogen, OH, $NH_2$, or SH;
$R^4$ is H, alkyl group or substituted alkyl group;
$X^1$-$X^2$ are independently selected from O, S, NH, H, alkyl, halogen, OH, SH, or $NH_2$;
W is a saturated acyclic hydrocarbon chain having 1 to 15 carbon atoms consisting essentially of hydrogen and carbon atoms;
Z is $CH_3$ or any neutral or positively charged group.

In another aspect there is provided, an antibiotic compound of formula (I):

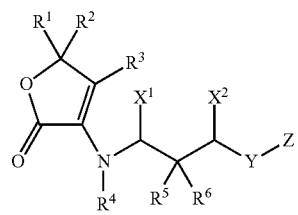

or a salt or stereoisomer thereof;
wherein $R^1$-$R^3$, $R^5$ and $R^6$ are independently selected from H, alkyl group, substituted alkyl group, halogen, OH, $NH_2$, or SH;
$R^4$ is H, alkyl group or substituted alkyl group;
$X^1$-$X^2$ are independently selected from O, S, NH, H, alkyl, halogen, OH, SH, or $NH_2$;
Y is an acyclic hydrocarbon chain having 2 to 20 carbon atoms or a substituted acyclic hydrocarbon chain having 2 to 20 carbon atoms with the proviso that Y does not include an oxygen atom;
Z is $CH_3$ or any neutral or positively charged group.

BRIEF DESCRIPTION OF THE DRAWINGS

FIG. 9 shows an effect of PEG-2 on *C. trachomatis* infection of HeLa cells.

treatment with 1 and 2.5 μM PEG-2S prevents changes of cytoplasmic pH (A) and [$Na^+$] (B) in HEK293 cells infected by *C. trachomatis* (plots are averages of 8 independent experiments with standard deviation shown, P<0.003).

Figure 23:
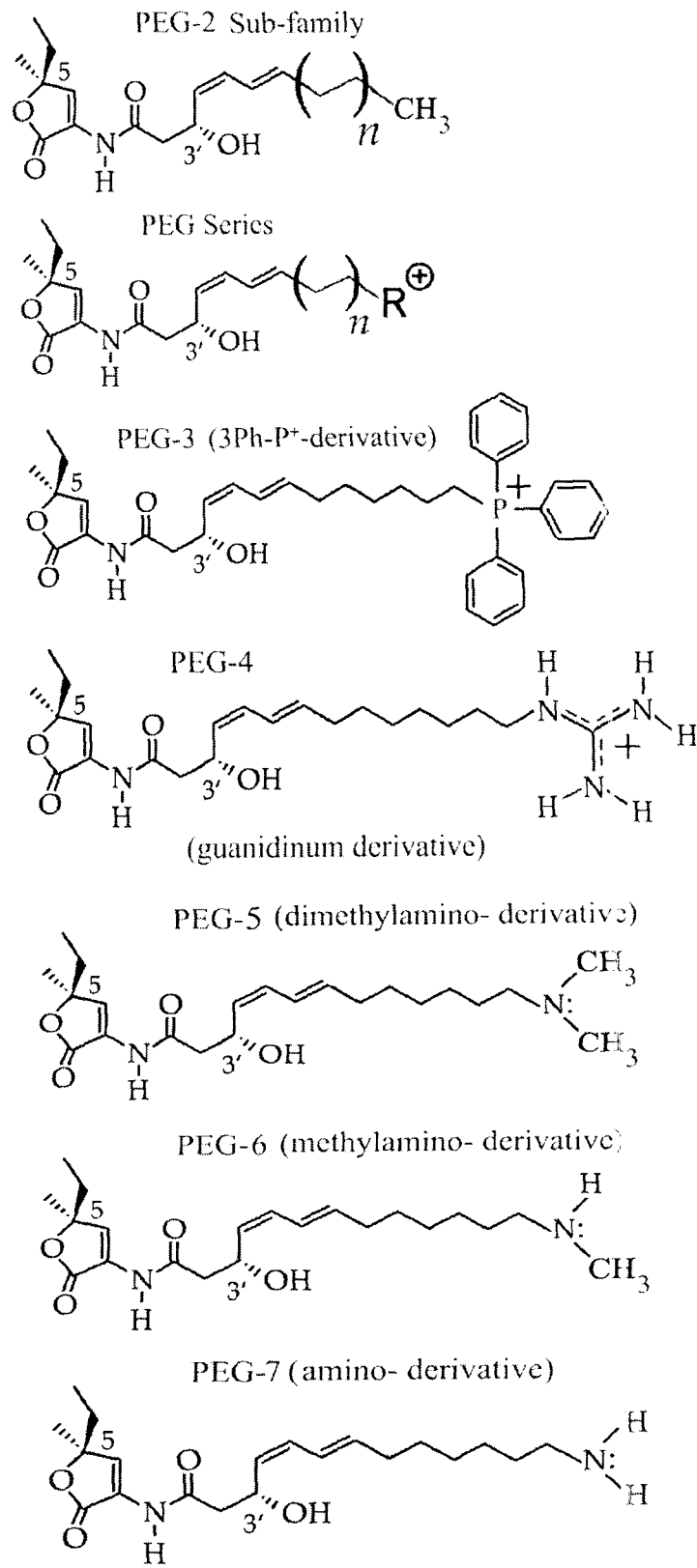

FIG. 23 shows examples of chemical structures of derivatives of PEG-2.

FIG. 24 shows that derivatives of PEG-2 provide an effective treatment against *C. trachomatis* infecting HeLa cells.

DETAILED DESCRIPTION OF PREFERRED EMBODIMENTS

Compounds, formulations, compositions, methods of treatment, and methods and systems of drug discovery described herein relate to formulae I, II, III, or IV, with formula I encompassing formulae II, III, or W, and formula III encompassing formula IV:

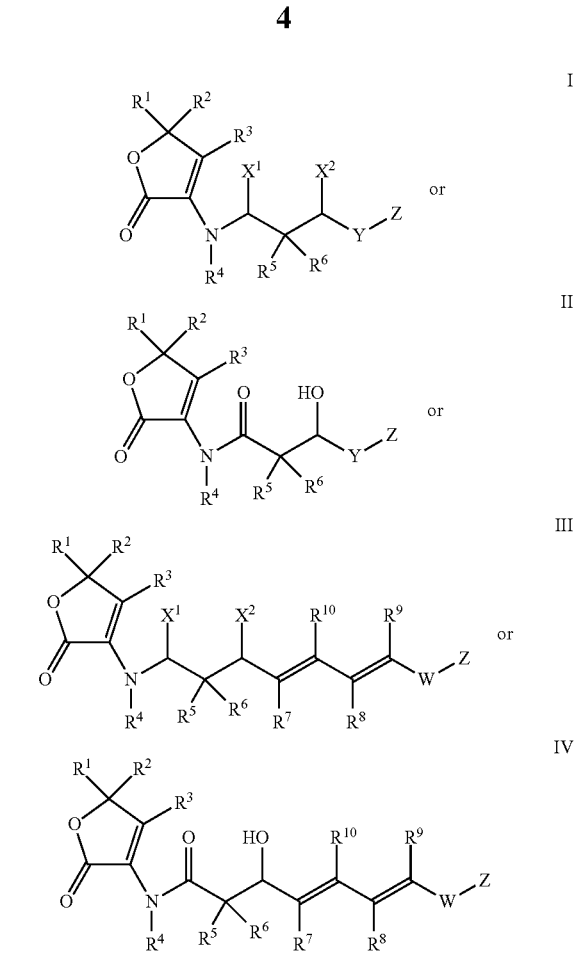

where $R^1$-$R^3$ and $R^5$-$R^{10}$ are independently selected from H, alkyl group, substituted alkyl group, halogen, OH, $NH_2$, or SH;

$R^4$ is H, alkyl group or substituted alkyl group;

$X^1$-$X^2$ are independently selected from O, S, NH, H, alkyl, halogen, OH, SH, or $NH_2$;

Y is an acyclic hydrocarbon chain having 2 to 20 carbon atoms or a substituted acyclic hydrocarbon chain having 2 to 20 carbon atoms;

W is an acyclic hydrocarbon chain having 1 to 15 carbon atoms or a substituted acyclic hydrocarbon chain having 1 to 15 carbon atoms;

Z is $CH_3$ or any neutral or positively charged group.

Formulae I, II, III and IV have in common a furanone ring N-linked to an acyclic side chain. As is apparent from formulae I, II, III and W both the furanone ring and the N-linked side chain can accommodate various substituents.

In certain embodiments, components of formulae I, II, III or W may be further defined. In one example, $R^1$-$R^{10}$ are independently selected from H or a C1-C5 alkyl group or a C1-C5 substituted alkyl group. In another example, $R^1$-$R^{10}$ are independently selected from H or a C1-C4 alkyl group or a C1-C4 substituted alkyl group. In another example, $R^1$-$R^{10}$ are independently selected from H or a C1-C3 alkyl group or a C1-C3 substituted alkyl group. In another example, $R^1$-$R^{10}$ are independently selected from H or a C1-C2 alkyl group or a C1-C2 substituted alkyl group. In another example, $R^4$ is H. In another example, $R^1$-$R^3$ are independently selected from H or C1-C2 alkyl, $R^5$-$R^{10}$ are independently selected from H or C1-C3 alkyl group, and $R^4$ is H.

In another example, $X^1$-$X^2$ are independently selected from O, S, H, C1-C3 alkyl, halogen, OH, SH. In another example, $X^1$-$X^2$ are independently selected from O, S, H, halogen, OH, SH. In another example, $X^1$-$X^2$ are independently selected from H, O, S, OH, or SH. In another example, $X^1$-$X^2$ are independently selected from H, O or OH. In another example, $X^1$ is O and $X^2$ is OH. In another example, $X^1$ is O and $X^2$ is H.

In another example, Y is an acyclic hydrocarbon chain having 4 to 20 carbon atoms or a substituted acyclic hydrocarbon chain having 4 to 20 carbon atoms. In another example, Y is an acyclic hydrocarbon chain having 2 to 14 carbon atoms or a substituted acyclic hydrocarbon chain having 2 to 14 carbon atoms. In another example, Y is an acyclic hydrocarbon chain having 2 to 12 carbon atoms or a substituted acyclic hydrocarbon chain having 2 to 12 carbon atoms. In another example, Y is an acyclic hydrocarbon chain having 2 to 10 carbon atoms or a substituted acyclic hydrocarbon chain having 2 to 10 carbon atoms. In another example, Y is an acyclic hydrocarbon chain having 2 to 8 carbon atoms or a substituted acyclic hydrocarbon chain having 2 to 8 carbon atoms. In another example, Y does not include an epoxide group. In another example, Y does not include a bromine group. In another example, Y does not include an oxygen atom. In another example, Y includes at least one carbon-carbon double bond. In another example, Y consists essentially of hydrogen and carbon atoms, encompassing variation that does not materially alter toxicity and expressly not including any epoxide group. In another example, Y consists only of hydrogen and carbon atoms.

In another example, W is an acyclic hydrocarbon chain having 1 to 12 carbon atoms or a substituted acyclic hydrocarbon chain having 1 to 12 carbon atoms. In another example, W is an acyclic hydrocarbon chain having 1 to 10 carbon atoms or a substituted acyclic hydrocarbon chain having 1 to 10 carbon atoms. In another example, W is an acyclic hydrocarbon chain having 1 to 8 carbon atoms or a substituted acyclic hydrocarbon chain having 1 to 8 carbon atoms. In another example, W is an acyclic hydrocarbon chain having 1 to 6 carbon atoms or a substituted acyclic hydrocarbon chain having 1 to 6 carbon atoms. In another example, W is an acyclic hydrocarbon chain having 1 to 4 carbon atoms or a substituted acyclic hydrocarbon chain having 1 to 4 carbon atoms. In another example, W does not include an epoxide group. In another example, W does not include a bromine group. In another example, W does not include an oxygen atom. In another example, W consists essentially of hydrogen and carbon atoms and is saturated, encompassing variation that does not materially alter toxicity and expressly not including any epoxide group. In another example, W consists only of hydrogen and carbon atoms.

In another example, Z does not include an epoxide group. In another example, Z does not include a bromine group. In another example, Z does not include an oxygen atom. In another example, Z is $CH_3$ or an organic group. In another example, Z is an organic group comprising a nitrogen atom. In another example, Z is an organic group comprising a phosphorus atom. In another example, Z is $CH_3$ or a positively charged organic group. In another example, Z is a halogen. In another example, Z is $CH_3$, a triphenylphosphine (3PhP) group, a guanidine group, an aminoperimidine group, an amiloride group or a halogen. In another example, the molecular weight of the compound is less than 2000 Daltons. In another example, the molecular weight of the compound is less than 1000 Daltons.

Figure 4:
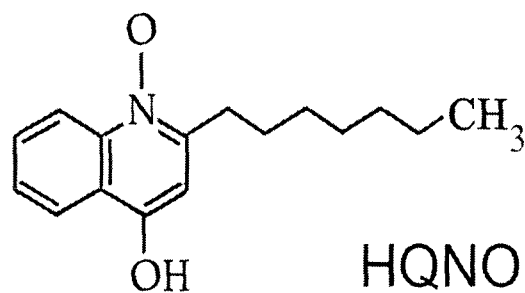
FIG. 4 shows a structural alignment comparison of korormicin and PEG-2.
Figure 4:
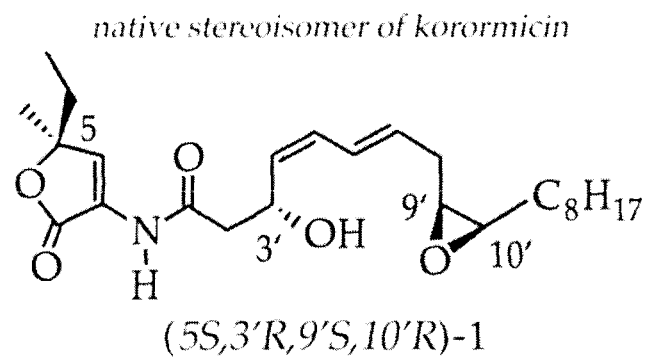
Figure 4:
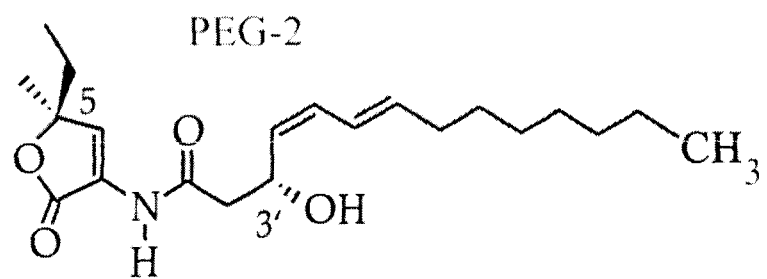

In another example, a compound of formulae I, II, III or IV will have at least two chiral centers, for example 5S and 3'R chiral centers shown in FIG. 4. In another example, a compound of formulae I, II, III or IV will have only two chiral centers, for example 5S and 3'R chiral centers shown in FIG. 4.

In another example, a compound of formulae I, II, III or IV is provided where $R^1$-$R^3$ are independently selected from H or a C1-C3 alkyl group and $R^5$-$R^{10}$ are independently selected from H or a C1-C5 alkyl group; $R^4$ is H; $X^1$-$X^2$ are independently selected from O, S, H, alkyl, halogen, OH, SH; Y is an acyclic hydrocarbon chain having 2 to 20 carbon atoms or a substituted acyclic hydrocarbon chain having 2 to 20 carbon atoms; W is an acyclic hydrocarbon chain having 1 to 15 carbon atoms or a substituted acyclic hydrocarbon chain having 1 to 15 carbon atoms; Z is a neutral or positively charged group comprising a nitrogen atom, and optionally the nitrogen atom forms a covalent bond with a carbon atom of Y or W.

In another example, a compound of formulae I, II, III or W is provided where $R^1$-$R^3$ are independently selected from H or a C1-C3 alkyl group and $R^5$-$R^{10}$ are independently selected from H or $CH_3$; $R^4$ is H; $X^1$-$X^2$ are independently selected from O, S, H, OH, or SH; Y is an acyclic hydrocarbon chain having 2 to 12 carbon atoms or a substituted acyclic hydrocarbon chain having 2 to 12 carbon atoms; W is an acyclic hydrocarbon chain having 1 to 8 carbon atoms or a substituted acyclic hydrocarbon chain having 1 to 8 carbon atoms; Z is a neutral or positively charged group comprising a nitrogen atom, and optionally the nitrogen atom forms a covalent bond with a carbon atom of Y or W.

In another example, a compound of formulae I, II, III or W is provided where $R^1$-$R^3$ are independently selected from H or a C1-C3 alkyl group and $R^5$-$R^{10}$ are independently selected from H or a C1-C5 alkyl group; $R^4$ is H; $X^1$-$X^2$ are independently selected from O, S, H, alkyl, halogen, OH, SH; Y is an acyclic hydrocarbon chain having 2 to 20 carbon atoms or a substituted acyclic hydrocarbon chain having 2 to 20 carbon atoms; W is an acyclic hydrocarbon chain having 1 to 15 carbon atoms or a substituted acyclic hydrocarbon chain having 1 to 15 carbon atoms; Z is a neutral or positively charged group comprising a phosphorus atom, and optionally the phosphorus atom forms a covalent bond with a carbon atom of Y or W.

In another example, a compound of formulae I, II, III or W is provided where $R^1$-$R^3$ are independently selected from H or a C1-C3 alkyl group and $R^5$-$R^{10}$ are independently selected from H or $CH_3$; $R^4$ is H; $X^1$-$X^2$ are independently selected from O, S, H, OH, or SH; Y is an acyclic hydrocarbon chain having 2 to 12 carbon atoms or a substituted acyclic hydrocarbon chain having 2 to 12 carbon atoms; W is an acyclic hydrocarbon chain having 1 to 8 carbon atoms or a substituted acyclic hydrocarbon chain having 1 to 8 carbon atoms; Z is a neutral or positively charged group comprising a phosphorus atom, and optionally the phosphorus atom forms a covalent bond with a carbon atom of Y or W.

In another example, a compound of formulae I, II, III or W is provided where $R^1$-$R^3$ are independently selected from H or a C1-C3 alkyl group and $R^5$-$R^{10}$ are independently selected from H or a C1-C5 alkyl group; $R^4$ is H; $X^1$-$X^2$ are independently selected from O, S, H, alkyl, halogen, OH, SH; Y is an acyclic hydrocarbon chain having 2 to 20 carbon atoms or a substituted acyclic hydrocarbon chain having 2 to 20 carbon atoms; W is an acyclic hydrocarbon chain having 1 to 15 carbon atoms or a substituted acyclic hydrocarbon chain having 1 to 15 carbon atoms; Z is halogen.

In another example, a compound of formulae I, II, III or W is provided where $R^1$-$R^3$ are independently selected from H or a C1-C3 alkyl group and $R^5$-$R^{10}$ are independently selected from H or CH$_3$; $R^4$ is H; $X^1$-$X^2$ are independently selected from O, S, H, OH, or SH; Y is an acyclic hydrocarbon chain having 2 to 12 carbon atoms or a substituted acyclic hydrocarbon chain having 2 to 12 carbon atoms; W is an acyclic hydrocarbon chain having 1 to 8 carbon atoms or a substituted acyclic hydrocarbon chain having 1 to 8 carbon atoms; Z is halogen.

In another example, a compound of formulae I, II, III or W is provided where $R^1$-$R^3$ are independently selected from H or a C1-C3 alkyl group and $R^5$-$R^{10}$ are independently selected from H or a C1-C5 alkyl group; $R^4$ is H; $X^1$-$X^2$ are independently selected from O, S, H, alkyl, halogen, OH, SH; Y is an acyclic hydrocarbon chain having 2 to 20 carbon atoms or a substituted acyclic hydrocarbon chain having 2 to 20 carbon atoms; W is an acyclic hydrocarbon chain having 1 to 15 carbon atoms or a substituted acyclic hydrocarbon chain having 1 to 15 carbon atoms; Z is CH$_3$.

In another example, a compound of formulae I, II, III or W is provided where $R^1$-$R^3$ are independently selected from H or a C1-C3 alkyl group and $R^5$-$R^{10}$ are independently selected from H or CH$_3$; $R^4$ is H; $X^1$-$X^2$ are independently selected from O, S, H, OH, or SH; Y is an acyclic hydrocarbon chain having 2 to 12 carbon atoms or a substituted acyclic hydrocarbon chain having 2 to 12 carbon atoms; W is an acyclic hydrocarbon chain having 1 to 8 carbon atoms or a substituted acyclic hydrocarbon chain having 1 to 8 carbon atoms; Z is CH$_3$.

Compounds described herein may be used to treat a subject or patient that is a human or non-human animal. Treatment of mammals is contemplated, including for example humans, primates, rodents, dogs, cats, cows, pigs, horses, or sheep. Contemplated treatment of birds include, for example, chicken or turkey.

"Treatment" or "treating" refers to therapy, prevention and prophylaxis and particularly refers to the administration of medicine or the performance of medical procedures with respect to a patient, for either prophylaxis (prevention) or to cure the infirmity or malady in the instance where the patient is afflicted.

"Therapeutic agent" refers to an agent capable of having a desired biological effect on a host. Antibiotic agents are an example of therapeutic agents that are generally known to be chemical in origin, as opposed to biological, typically having a small molecule structure with a molecular weight of less than 2000 Daltons.

The term "therapeutically effective amount" refers to that amount of an agent, modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process.

Modulators include, for example, a polypeptide, nucleic acid, macromolecule, complex molecule, small molecule, compound, species or the like (naturally-occurring or non-naturally-occurring), or an extract made from biological materials such as bacteria, plants, fungi, or animal cells or tissues, that may be capable of causing modulation.

Modulators may be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators may be screened at one time. The activity of a modulator may be known, unknown or partially known.

Dosage ranges for the administration of antibiotic compounds are readily determined by the skilled person through routine testing. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications.

The dose, schedule of doses and route of administration may be varied, whether oral, nasal, vaginal, rectal, extraocular, intramuscular, intracutaneous, subcutaneous, or intravenous, and the like.

Antibiotic compounds described herein can be used therapeutically in combination with a pharmaceutically acceptable carrier. Pharmaceutically acceptable refers to those ingredients, compositions and dosages thereof within the scope of sound medical judgment, suitable for use in contact with the tissues of human beings and animals without excessive toxicity, irritation, allergic response, or other problem or complication, commensurate with a reasonable benefit/risk ratio. Pharmaceutically acceptable carriers are known to those skilled in the art. These most typically would be standard carriers for administration of compositions to humans, including solutions such as sterile water, saline, and buffered solutions at physiological pH.

Pharmaceutically acceptable carriers include liquid carriers, solid carriers, or both. Liquid carriers include, but are not limited to, water, saline, physiologically acceptable buffers, aqueous suspensions, oil emulsions, water in oil emulsions, water-in-oil-in-water emulsions, site-specific emulsions, long-residence emulsions, sticky-emulsions, microemulsions and nanoemulsions. Examples of aqueous carriers include water, saline and physiologically acceptable buffers. Examples of non-aqueous carriers include a mineral oil or a neutral oil including, but not limited to, a diglyceride, a triglyceride, a phospholipid, a lipid, an oil and mixtures thereof. Solid carriers are biological carriers, chemical carriers, or both and include, for example, particles, microparticles, nanoparticles, microspheres, nanospheres, minipumps, bacterial cell wall extracts, and biodegradable or non-biodegradable natural or synthetic polymers that allow for sustained release of the composition Molecules intended for pharmaceutical delivery may be formulated in a pharmaceutical composition. Pharmaceutical compositions may include acceptable carriers, thickeners, diluents, buffers, preservatives, surface active agents and the like in addition to the molecule of choice. Pharmaceutical compositions may also include one or more active ingredients having biological activity such as antimicrobial agents, anti-inflammatory agents, anesthetics, allergy relief agents, pain relief agents and the like.

A composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The compositions may be administered according to standard procedures used by those skilled in the art.

An effective dose or amount, and any possible effects on the timing of administration of the formulation, may need to be identified for any particular compound described herein. This may be accomplished by routine experiment, using one or more groups of animals (for example using at least 5 animals per group), or in human trials if appropriate. The effectiveness of any compound and method of treatment or prevention may be assessed by administering the compound and assessing the effect of the administration by measuring one or more indices associated with the disease or condition of interest, and comparing the post-treatment values of these indices to the values of the same indices prior to treatment.

The precise time of administration and amount of any particular compound that will yield the most effective treatment in a given patient may depend upon the activity, pharmacokinetics, and bioavailability of a particular compound, physiological condition of the patient (including age, sex, disease type and stage, general physical condition, responsiveness to a given dosage and type of medication), route of administration, and the like.

While a subject is being treated, the health of the subject may be monitored by measuring one or more of the relevant indices at predetermined times during a 24-hour period. Treatment, including supplement, amounts, times of administration and formulation, may be optimized according to the results of such monitoring. The subject may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of two weeks being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds described herein, or alternatively other antibiotic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the LD50 and the ED50. Compositions that exhibit large therapeutic indices are advantageous. Although compounds that exhibit toxic side effects may be used, care should be taken to design dosage ranges, formulations, or delivery systems that target the compounds to the desired site in order to reduce side effects.

The data obtained from the cell culture assays and non-human animal studies may be used in formulating a range of dosage for use in humans. The dosage of any supplement, or alternatively of any components therein, can lie within a range of circulating concentrations that include the ED50 with little or no toxicity. The dosage may vary within this range depending upon the dosage form employed and the route of administration utilized. For agents described herein, the therapeutically effective dose may be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Compounds described herein may be used for antibiotic treatment of a subject or patient that is a human or non-human animal. The antibiotic treatment can be useful in inhibiting growth of various bacteria and modulating bacterial infections. Without wishing to be bound by theory, the antibiotic treatment may include an interaction with an $Na^+$-translocating NADH: ubiquinone oxidoreductase ($Na^+$-NQR) protein or peptide and/or may include modulation of $Na^+$-NQR activity.

Without wising to be bound by theory, the present inventors have developed a model for explaining how the $Na^+$ cycle and sodium motive pumps may play a role in the course of bacterial infection. Specifically, the model suggests targeting the $Na^+$-translocating NADH: ubiquinone oxidoreductase ($Na^+$-NQR) in bacteria as a mechanism to control bacterial replication and viability. $Na^+$-NQR is an unusual respiratory enzyme that functions as a primary sodium pump utilizing the energy of oxidation of NADH by quinone to expel $Na^+$ ions from the cytoplasm. It thus creates a sodium motive force that can be directly used for metabolic work, including import of amino acids and operation of multidrug resistance pumps. Importantly, $Na^+$-NQR is present in many pathogenic bacteria, but it is absent in mitochondria of human cells as well as in the species belonging to normal gastroenteric microflora. Thus, specific targeting of this enzyme may result in less non-specific side effects in human cells and normal gastoenteric microflora than traditionally prescribed antibiotics.

The mechanistic pathway and the involvement of $Na^+$-NQR in bacterial metabolism can occur in several steps. The consumption of any available intracellular ATP by intruding bacteria results in a slowing of $Na^+$ pump which can decelerate the removal of $Na^+$ from the infected cell. Stimulation of glycolysis by the invading bacteria can accentuate the $Na^+$ overload indirectly by causing an acidification of the cytoplasm which ultimately activates the $Na^+/H^+$ exchanger (NHE1) to import more $Na^+$ into the cell in exchange for the removal of intracellular $H^+$. When intracellular pools of ATP and glucose are exhausted, the pathogenic bacteria can switch to amino acid catabolism, which efficiently raises the pH of the cytoplasm. Intracellular concentration of $Na^+$ ions remains elevated due to the depressed activity of the $Na^+$ pump. $Na^+$-NQR is an unusual respiratory enzyme that functions as a primary sodium pump utilizing the energy of oxidation of NADH by quinone to expel $Na^+$ ions from the cytoplasm. It thus creates a sodium motive force that can be directly used for metabolic work, including import of amino acids and operation of multidrug resistant pumps. Under these conditions, the pathogenic bacteria rely on the $Na^+$-NQR to energize the uptake of amino acids, which can occurs via several pathways including $Na^+$-amino acid symports. Inhibition of $Na^+$-NQR should, therefore, under these conditions result in no ability to provide energy to support amino acid uptake over to re-establish normal ionic homeostasis.

Na⁺-NQR, is the major respiratory Na⁺ pump in aerobic pathogens. Phylogenetic analysis shows that variants of full Na⁺-cycle as well as sole primary Na⁺ pumps are overrepresented in pathogenic species, possibly due to the difficulties for the intruding pathogens to maintain sufficiently high proton-motive force (PMF) in hostile microenvironments of a colonized macro-organism. Widespread distribution of Na⁺-NQR and its implication in the regulation of virulence traits make this enzyme an attractive candidate for the development of novel antibiotics, especially after recent long-awaited breakthrough in studies of Na⁺-NQR structure (Steuber et al. Structure of the *V. cholerae* Na⁺-pumping NADH:quinone oxidoreductase. Nature. 2014; 516:62-67).

Na⁺-NQR is found in a number of pathogenic bacteria. The potential for it to affect the course of a wide range of pathogenic bacteria is, therefore, large. Potentially, any Na⁺-NQR-containing pathogenic bacterium could be sensitive to drugs targeting Na⁺-NQR. An incomplete and illustrative list of the many species that contain Na⁺-NQR and the diseases with which these bacteria are associated is shown in Table 1.

TABLE 1

Na⁺-NQR-containing bacteria and the diseases associated with these infections.

| ORGANISM | Gram | DISEASE(S) CAUSED |
|---|---|---|
| *Vibrio cholerae* | (−) | (cholera) |
| *Vibrio parahaemolyticus* | (−) | (acute gastroenteritis) |
| *Vibrio vulnificus* | (−) | (ulcers, GE infections) |
| *Vibrio gastroenteritis* | (−) | (acute gastroenteritis) |
| *Vibrio damsela* | (−) | (wound infection, septicemia) |
| *Vibrio fluvialis* | (−) | (foodborne diarrhea) |
| *Vibrio furnissii* | (−) | (foodborne diarrhea) |
| *Vibrio harveyi* | (−) | (foodborne diarrhea) |
| *Vibrio hollisae* | (−) | (foodborne diarrhea) |
| *Vibrio costicola* | (−) | (foodborne diarrhea) |
| *Vibrio mimicus* | (−) | (foodborne diarrhea) |
| *Vibrio cincinnatiensis* | (−) | (foodborne diarrhea) |
| *Aeromonas veronii* | (−) | (wound infection, diarrhea) |
| *Aeromonas caviae* | (−) | (gastroenteritis) |
| *Legionella pneumophila* | (−) | (Legionnaires' disease) |
| *Treponema denticola* | (−) | (necrotizing gingivitis) |
| *Porphyromonas gingivalis* | (−) | (adult periodontitis) |
| *Tannerella forsythia* | (−) | (periodontitis) |
| *Actinobacillus actinomycetemcomitans* | (−) | (juvenile periodontitis) |
| *Neisseria meningitides* | (−) | (meningitides) |
| *Neisseria gonorrhoeae* | (−) | (gonorrhea) |
| *Neisseria sicca* | (−) | (pneumonia, endocarditis) |
| *Haemophilus influenzae* | (−) | (pneumoniae, otitis) |
| *Haemophilus ducreyi* | (−) | (chancroid) |
| *Pseudomonas aeruginosa* | (−) | (lung and skin infections) |
| *Pseudomonas pseudoalcaligenes* | (−) | (peritonitis) |
| *Photorhabdus asymbiotica* | (−) | (lesions) |
| *Salmonella enterica* (s. Paratyphi) | (−) | (paratyphoid fever) |
| *Salmonella enterica* (s. Typhi) | (−) | (typhoid fever) |
| *Klebsiella pneumoniae* | (−) | (pneumonia) |
| *Yersinia pestis* | (−) | (plague) |
| *Yersinia pseudotuberculosis* | (−) | (Far East scarlet-like fever) |
| *Chlamydophila pneumoniae* | (−) | (bronchitis, pneumonia) |
| *Chlamydia trachomatis* | (−) | (trachoma, vaginitis) |
| *Simkania negevensis Z* | (−) | (juvenile pneumoniae and acute bronchiolitis) |
| *Waddlia chondrophila* | (−) | (human fetal death) |
| *Pasteurella multocida* | (−) | (lesions) |
| *Serratia proteamaculans* | (−) | (pneumonia) |
| *Bacteroides fragilis* | (−) | (peritoneal infections) |
| *Moraxella catarrhalis* | (−) | (respiratory, middle ear, eye, CNS infections) |

Illustrative examples of Na⁺-NQR-containing pathogens are found among beta- and gamma-proteobacteria (Enterobacteriales, Vibrionalles, Pasteurellales, Aeromonadales, Pseudomonadales, Neisserales), Bacteroidetes and Chlamydiae (Chlamydiae may have received Na⁺-NQR by horizontal gene transfer).

Gram-positive Clostridiae (*Clostridium difficile* and other pathogenic Clostridiae such as *C. perfringens* (Gangrene, Food poisoning), *C. tetani* (Tetanus), *C. botulinum*) have an ancestral form of the Na⁺-NQR enzyme, termed RFN. RFN contains a subunit RfnD, which is homologous to the NqrB (targeted by korormicin), but a Gly140-Gly141 pair from NqrB is not conserved in RfnD.

For illustrative purposes a compound with a furanone ring and N-linked substituted hydrocarbon chain as characterized by a compound of formula I, II, III or IV has been chemically synthesized and tested for antibiotic activity in a first set of experimental examples. The compound is referred to as PEG-2 and its chemical structure is:

PEG-2

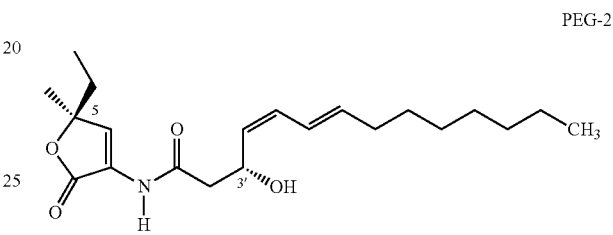

Demonstration of PEG-2 antibiotic activity was carried out in a model assay of *Chlamydia trachomatis* infection of HeLa cells. PEG-2 activity was also compared to korormicin and various homoserine lactones. This first set of experimental examples are for illustration purposes only and is not intended to be a limiting description.

*Chlamydia trachomatis* (*C. trachomatis*) propagation and treatment were carried out as follows. *C. trachomatis* was propagated in HeLa cells. The titer of *C. trachomatis* was determined in cyclohexamide-treated HeLa cells, and concentrations used were expressed as inclusion forming units (IFU) per mL.

PEG-2 was solubilized in DMSO in (stock concentration 50 mM). During the treatment with PEG-2 subsequent dilutions were made and corresponding amount of DMSO was always added to controls.

Cell Toxicity Assay was performed as follows. HeLa, HEK293 and primary VSM cells were seeded at $5 \times 10^3$ cells/well in 96-well plates and incubated with Korormicin, PEG-2 or homoserine lactones in DMEM containing 1% fetal bovine serum (FBS; Invitrogen Corp.). After 48 hours, the number of living cells was determined by a colorimetric enzyme assay, based on a cytoplasmic enzyme activity present in viable cells.

Assessment of the level of infection was determined as follows. HeLa cells were seeded on glass coverslips in 24-well plates at $3 \times 10^4$ cells/well and inoculated with *C. trachomatis* and then treated with antibiotic (or other compounds of interest). After 48 hours, the infected cells were fixed with 100% methanol and then incubated with anti-*Chlamydia* monoclonal antibody. Inclusion bodies were visualized by staining with FITC-conjugated secondary antibody and DAPI as counterstaining. The samples were examined by a fluorescence microscopy. Number of inclusions was calculated per 100 cells.

Figure 1:
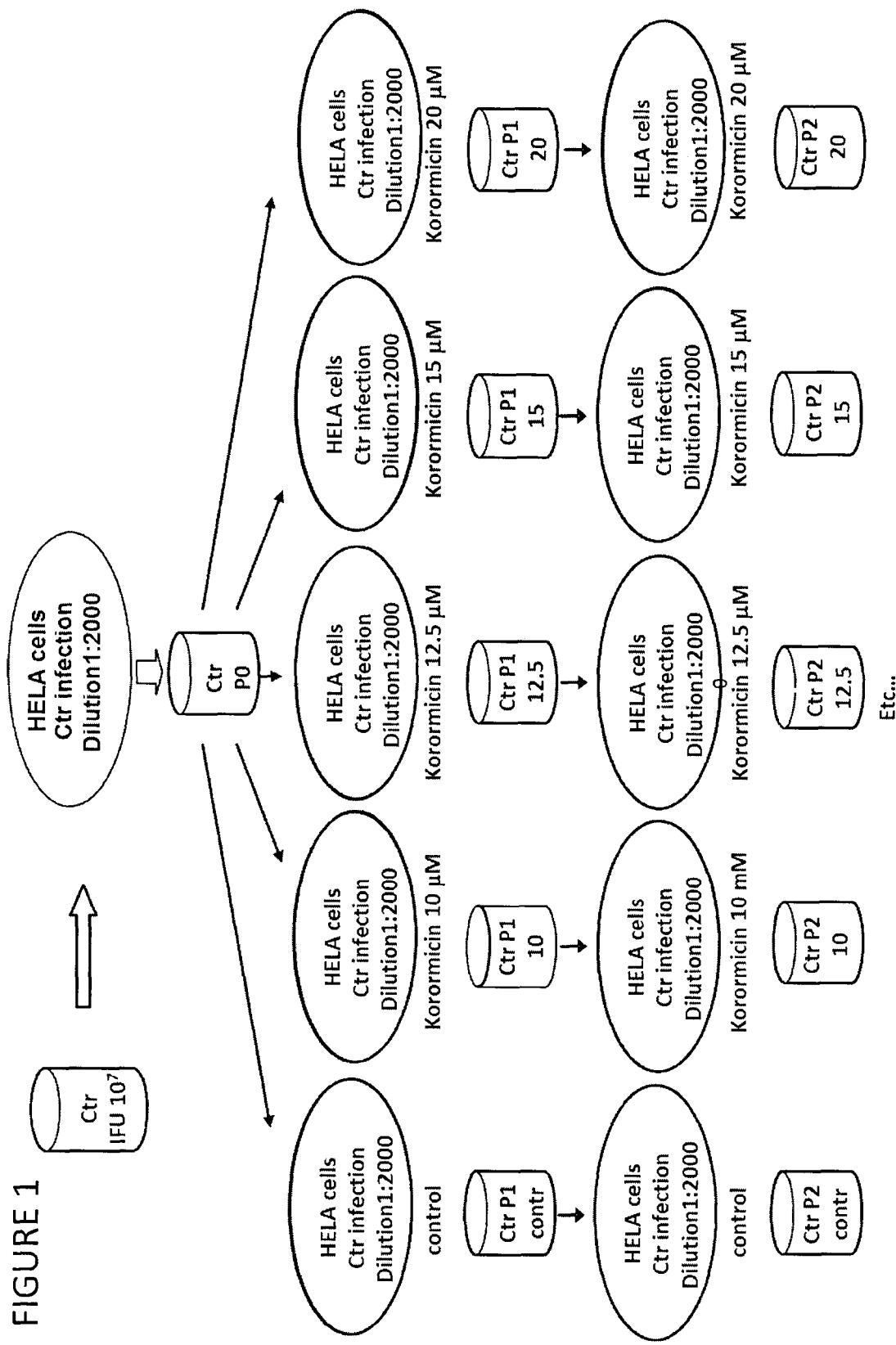
FIG. 1 shows an experimental design for assessment of an effect of korormicin on *C. trachomatis* infection of human cells.
Figure 2:
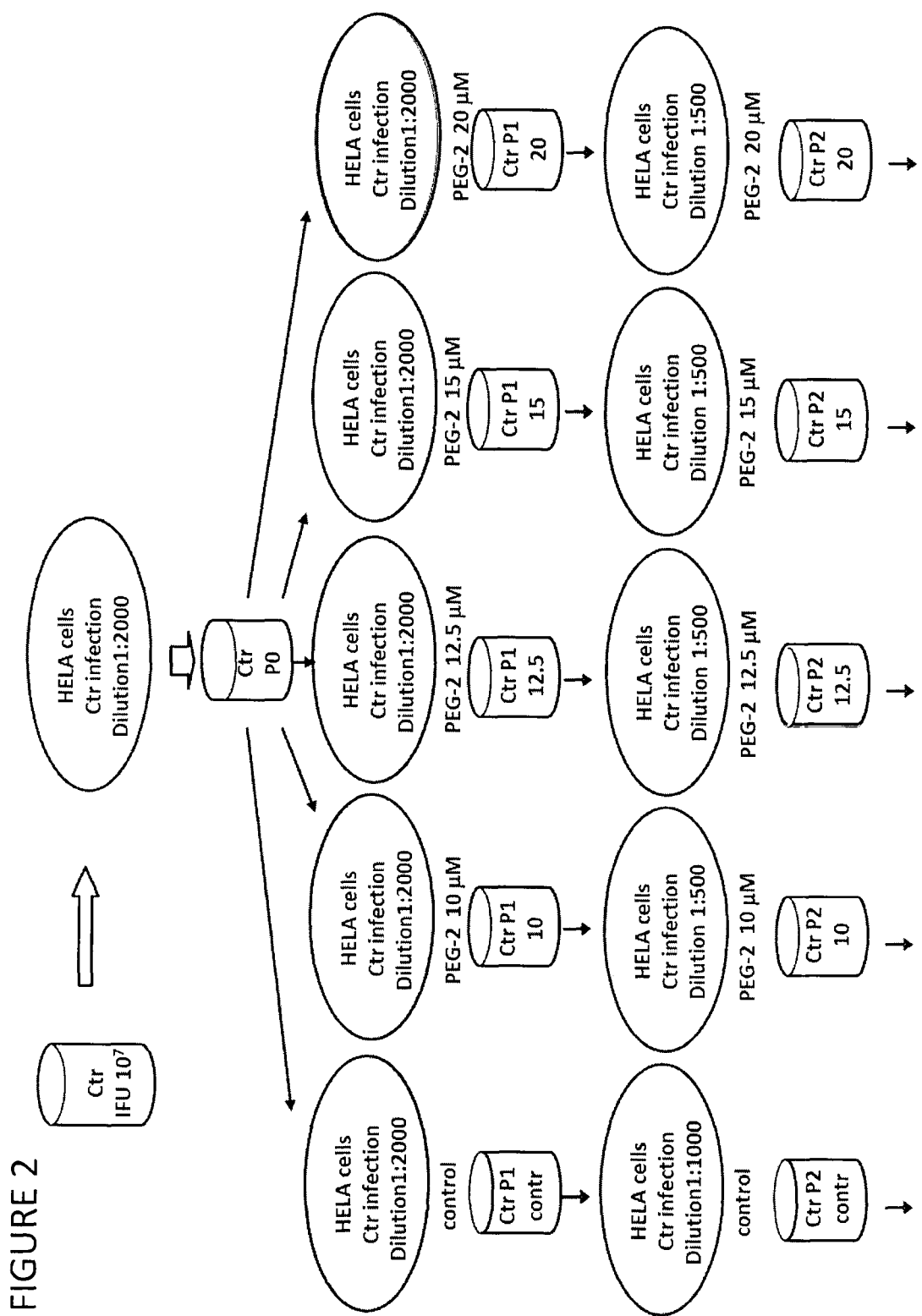
FIG. 2 shows an experimental design for assessment of an effect of PEG-2 on *C. trachomatis* infection of human cells.
Figure 2:
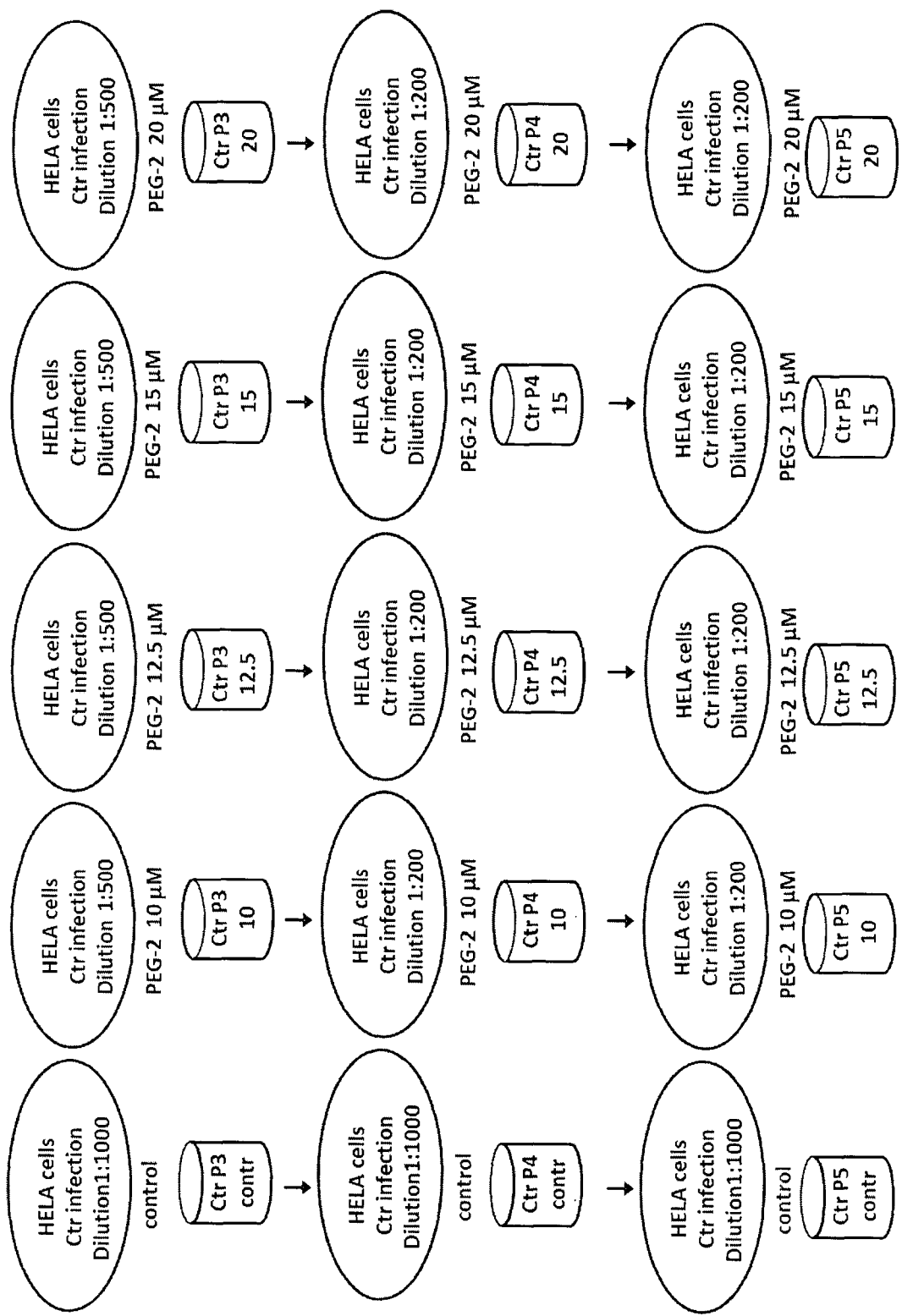
Figure 3:
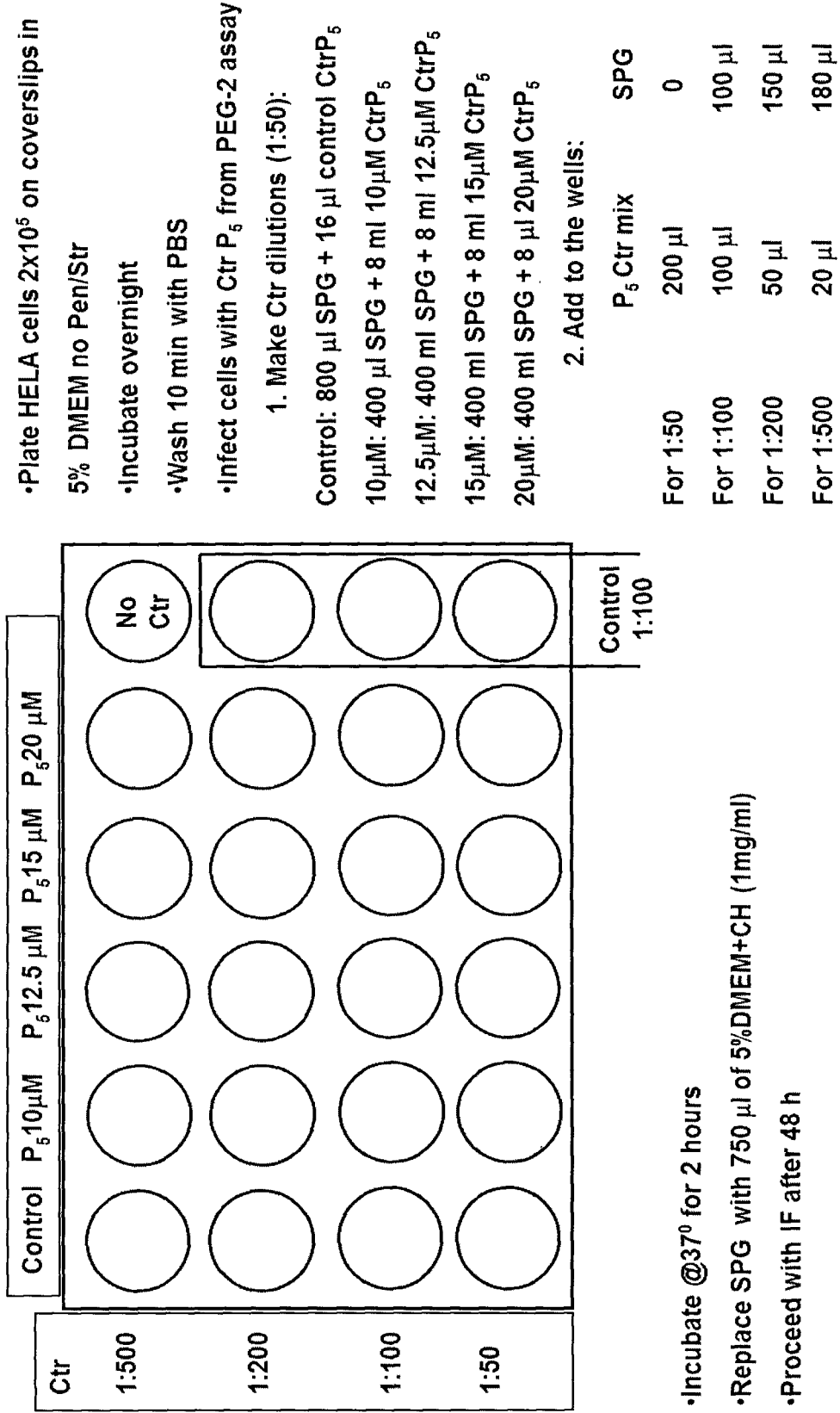
FIG. 3 shows an experimental design for titration of P5 PEG-2 treatments shown in FIG. 2.

Assessment of antichlamydial activity of Korormicin (Scheme shown in FIG. 1) and PEG-2 (Scheme shown in FIG. 2) were performed as follows. Cells were infected with *C. trachomatis* and treated with different concentrations of antibiotic of choice. After 48 h of *C. trachomatis* was collected (P1) and used to infect fresh cells. Subsequent collections of *C. trachomatis* were used to obtain P2, P3, P4 and P5 stocks of *C. trachomatis*. Dilution of *C. trachomatis* used to infect cells after treatment with PEG-2 had to be minimized in order to visualize inclusions. (See scheme shown in FIG. 2). Last passage collection of *C. trachomatis* (P5) of Korormicin treatment and all collected of passages of *C. trachomatis* treated with PEG-2 were used to establish infectivity of treated *Chlamydia* (Scheme shown in FIG. 3).

A comparison of the korormicin and PEG-2 structures is shown in FIG. 4. PEG-2 is a molecule which is a derivative of korormicin with the epoxy group removed.

In 1997, Yoshikawa et al. (Japanese Patent 3905604B2 published 18 Apr. 2007) isolated korormicin from the marine bacterium *Pseudoalteromonas* sp. F-420, and demonstrated an inhibitory activity of korormicin against the growth of gram-negative marine *Vibrios*. Korormicin is the best, most specific inhibitor currently available to inhibit the $Na^+$-NQR. Korormicin is a specific, very potent inhibitor of quinone reduction by $Na^+$-NQR with the inhibitor constant of 82 pM (while HQNO has a Ki of 300 nM). Both HQNO and korormicin have a common binding site in the $Na^+$-NQR complex (mutually exclusive inhibitors). This indicates a possible accessibility problem in that only traces of the added antibiotic actually reach its target ($Na^+$-NQR). Furthermore, koromicin has never been developed for use in animals, more particularly mammals, and even more particularly humans. Thus, a first experimental goal was to determine the efficacy of korormicin against an intracellular infection of animal cells, for example human cells. A second experimental goal was to design an alternative to koromicin, and compare toxicity and/or efficacy results in the context of an intracellular infection of animal cells, for example human cells.

FIGS. 5 and 6 show that korormicin is effective against *C. trachomatis* infection of eukaryotic cells, more particularly human cells. However, these concentrations of korormicin in cell culture model are ~10,000 fold higher (micromolar range) than in preparations of isolated $Na^+$-NQR (Ki of ~80 pM). Thus, these results appear to confirm the hypothesized accessibility problem. Furthermore, FIG. 7 shows that korormicin is toxic to the primary cells at the same concentrations in which it shows an antibiotic action. The toxicity problem of korormicin with respect to an animal cell, more particularly a human cell, is a novel finding that was previously unrecognized and has never been documented in prior published literature. These data clearly demonstrate that native korormicin is not useful as an antibiotic for treatment in humans.

FIG. 8 shows that PEG-2 is non-toxic to eukaryotic cells, more particularly human cells. Furthermore, examination of HeLa and HEK293 cell lines as well as primary Vascular Smooth Muscle cells have found no toxic effects at PEG-2 concentrations of up to 50 μM (not shown).

FIGS. 9 through 13 show that PEG-2 is effective as an antibiotic against *C. trachomatis* infection of eukaryotic cells, more particularly human cells. Moreover, FIG. 14 shows that PEG-2 is almost 1,000 times more effective as an antichlamydial agent than native korormicin. Thus, PEG-2 improves upon korormicin for both toxicity and efficacy for antibiotic treatment of microbial infections of human cells. In addition, PEG-2 represents an excellent platform for further drug design.

The possibility that homoserine lactones may function as antibiotics in eukaryotes was also studied. Representative homoserine lactones are shown in FIG. 15. The results provided in Table 2 show that the homoserine lactones tested are either highly toxic (N-3-oxo-dodecanoyl-L-Homoserine lactone) to human cells or ineffective (the other three homoserine lactones) as anti-chlamydial agents. These results suggest that the furanone ring of PEG-2 may be a significant contributor to the efficacy of PEG-2 antibiotic activity.

TABLE 2

Effects of homoserine lactones on HeLa cell viability and anti-Chlamydia trachomatis efficacy.

| | | Cytotoxicity of PEG-2 (concentration in μM) On HeLa cell line | | | | Anti-Chlamydial effect of PEG-2 (concentration in μM) | | | |
|---|---|---|---|---|---|---|---|---|---|
| Name | Formula | 12.5 | 25 | 50 | 100 | 12.5 | 25 | 50 | 100 |
| N-decanoyl-L-Homoserine lactone | $C_{14}H_{25}NO_3$ | no | no | no | no | no | no | no | no |
| N-butyryl-L-Homoserine lactone | $C_8H_{13}NO_3$ | no | no | no | no | no | no | No | no |
| N-3-oxo-dodecanoyl-L-Homoserine lactone | $C_{16}H_{27}NO_4$ | yes | yes | yes | yes | n/a | n/a | n/a | n/a |
| N-hexanoyl-L-Homoserine lactone | $C_{10}H_{17}NO_3$ | no | no | no | no | no | no | No | no |

The mechanism of action of PEG-2 was also investigated by monitoring intracellular acidification of infected cells treated with PEG-2. If PEG-2 is working through the inhibition of $Na^+$-NQR and a sodium motive force, then it would be expected to have an effect on intracellular $Na^+$ and $H^+$ concentrations within infected cells. HeLa cells were infected with *C trachomatis* and intracellular acidification was monitored with fluorescent indicator dyes.

*C. trachomatis* infection of a eukaryotic cell in culture acidifies the cytoplasm of the host cell at the onset of infection. As shown in FIGS. 16 and 17, PEG-2 can delay the initial *C. trachomatis*-induced acidification by at least 2 hours and diminishes the following acidification.

Both of these effects on intracellular $H^+$ are consistent with the proposed action of energy metabolism identified for a pathogenic bacterial infection and PEG-2's molecular mechanism of action through the inhibition of $Na^+$-NQR activity.

Further synthesis of PEG molecules, including a stereoisomer of PEG-2, have been achieved and tested experimentally to demonstrate antibiotic activity in a second set of experimental examples. In this second set of experimental examples PEG-2 is the non-stereospecific furanone antibiotic described above in the first set of experimental examples, while PEG-2S is a corresponding stereospecific furanone antibiotic. The following second set of experimental examples are for illustration purposes only and are not intended to be a limiting description.

Assays of the Growth of Free-Living Bacteria.

Effect of the synthetic $Na^+$-NQR inhibitor, PEG-2, on growth of *E. coli*, *L. lactis*, and *E. faecalis* was assayed as follows. Overnight starter cultures were grown aerobically in standard tryptic soy broth (TSB, Difco) and used to inoculate 200 µl TSB medium in 96-deep-well plates (Whatman) at an initial OD600 of 0.05. The obtained cultures were supplemented with 0.5, 1.0, 2.0, 5.0, 10.0, 20.0, and 50.0 µM PEG-2 (or pure DMSO in "zero" controls) and grown at 37° C. for 24 h with vigorous aeration. At 6, 18, and 24 h, growth was measured as OD600 by scanning the plates on a Bio-Rad iMark microplate reader. For samples taken at 18 and 24 h, serial dilutions with the pre-warmed growth medium were prepared using the aliquots of bacterial cultures. The experiments were repeated at least three times.

Evaluation of a PEG-2S against *Clostridium difficile* (*C. difficile* ATCC 700057) was performed by Drop method on pre-reduced BAK plates according to *Performance Standards for Antimicrobial Susceptibility Testing* (Methods for Antimicrobial Susceptibility Testing of Anaerobic Bacteria; Approved Standard—Eighth Edition; Volume 32 Number 5, 2012).

Assessment of Antichlamydial Properties of Antibiotics.

For MIC50 (Minimal Concentration of the antibiotic that inhibits formation of chlamydial incluions on 50%) determination HeLa cells were grown in 24-well or 96 well plates overnight prior to chlamydial inoculation. Elementary bodies were applied to the cells in small volume of SPG (0.22 M sucrose, 8.6 mM $Na_2HPO_4$, 3.8 mM $KH_2PO_4$, 5 mM glutamic acid, 0.2 µm-filtered, pH 7.4) and after 2 hours of incubation unattached elementary bodies were removed and infected cells were treated with different concentration of antibiotics in Dulbecco's modified Eagle's medium (DMEM, Invitrogen) with 5% fetal bovine serum (FBS, Invitrogen) in the presence of cycloheximide (1.0 µg/ml). After 42 h inclusions were visualized by immunocytochemistry.

To determent chlamydicidal effect of Korormicin (Scheme 1) and PEG-2 (Scheme 2) Hela cells were infected with *C. trachomatis* and treated with different concentrations of antibiotics. After 48 h of *C. trachomatis* was collected (P1) and used to infect fresh cells. Subsequent collections of *C. trachomatis* were used to obtain P2, P3, P4 and P5 stocks of *C. trachomatis*. Dilution of *C. trachomatis* used to infect cells after treatment with PEG-2 had to be minimized in order to visualize inclusions. (See Scheme 2 below). Last passage collection of *C. trachomatis* (P5) of Korormicin treatment and all collected of passages of *C. trachomatis* treated with PEG-2 were used to establish infectivity of treated *C. trachomatis*. Minimal chlamydicidal concentration (MCC2) for Korormicin, PEG-2 and PEG-2S was calculated after 2 passages of infection with treatment and reflect inhibition of infection for more than 90%. In all experiments inclusions were visualized by immunocytochemistry.

Immunocytochemistry.

Cells were seeded on glass coverslips in 24-well plates (2-4×10$^4$ cells/well) or on glass-bottom 96 well plates (10$^4$ cells/well), and after overnight inoculated with *C. trachomatis*. After 42 hours, the infected cells were fixed with 90% acetone (or 100% methanol in case of 96 well plates) and then incubated with anti-*Chlamydia* antibody (Thermo Fisher Scientific). Alexa Fluor 488-conjugated anti-rabbit IgG (Molecular Probes) was used as secondary antibody. DAPI staining solution (300 nM) was added to the coverslips to identify nuclei. Inclusion bodies were visualized using a fluorescent inverted microscope (TE-2000s; Nikon) Cells and inclusions were counted using Adobe Stock Photos CS3.Ink software.

Cell Proliferation Assay.

Cells were seeded at 5×10$^3$ cells/well in 96-well plates and incubated with *C. trachomatis* in DMEM containing 1% fetal bovine serum (FBS; Invitrogen Corp.). After 48 hours, the number of living cells was determined by a colorimetric enzyme assay (CellTiter 96 Cell Proliferation Assay; Promega Corporation, Madison, Wis.) based on a cytoplasmic enzyme activity present in viable cells. (Cory et al. *Use of an aqueous soluble tetrazolium/formazan assay for cell growth assays in culture. Cancer Commun.* 1991; 3:207-212). The absorbance of a formazan product in tissue culture media was measured at 500 nm using a microplate reader.

Preparation of Sub-Bacterial Membrane Vesicles from *V. cholerae* Cells.

Membrane vesicles from *V. cholerae* strains were prepared as described previously (Dibrov et al. Chemiosmotic mechanism of antimicrobial activity of $Ag^+$ in *Vibrio cholerae*. Antimicrob Agents Chemotherapy. 2002; 46:2668-2670) with some modifications. Mid-log cells were harvested by centrifugation, washed once and resuspended in Buffer A containing 100 mM KCl, 50 mM NaCl, 5 mM $MgSO_4$, 20 mM HEPES-Tris, pH 8.0. The cells were disrupted by a passage through the French press (Aminco) at 16,000 psi. Unbroken cells and cell debris were removed by low-speed centrifugation, and the vesicles were collected after centrifugation of the supernatant at 180,000 g for 90 min. The membrane pellet was suspended in buffer A at 20-30 mg protein/mL, snap-frozen in liquid nitrogen and stored at minus 80 degrees C. until use. Protein content in sub-bacterial vesicles was determined by the Bio-Rad Detergent Compatible Protein Assay Kit.

$Na^+$-NQR Activity Assays in Sub-Bacterial Vesicles.

Membranes of *V. cholerae* contain two enzymes capable of NADH oxidation: $Na^+$-NQR and NDH-2 (non-coupled NADH:ubiquinone oxidoreductase of type 2), but only $Na^+$-NQR is able to oxidize dNADH (deamino-NADH or nicotinamide hypoxanthine dinucleotide). Activity of $Na^+$-NQR in sub-bacterial *V. cholerae* vesicles was measured at 25 degrees C. as oxidation of dNADH ($\varepsilon_{340}$=6.22 mM$^{-1}$ cm$^{-1}$) by following the changes in its fluorescence at 440 nm (excitation light λ=340 nm) using Shimadzu RF-1501 spectrofluorometer. The assays were conducted in Buffer A supplemented with 15 µM $Na^+$-dNADH with constant stirring. The reaction was initiated by the addition of vesicles (aliquots of 50 µg of protein). Calibration assays confirmed that fluorescence at 440 nm, as a function of [dNADH] in the experimental buffer was linear up to 20 µM of added dNADH (not shown).

Measurements of Intracellular pH and Sodium in Cell Cultures.

pHrodo™ Green AM and CoroNa Green Sodium Indicator (both Molecular Probes, Invitrogen) were used to measure intracellular pH ($pH_i$) and intracellular sodium ($Na^+_i$) concentration. HEK293 cells were seeded on 24 well plates and infected with *C. trachomatis* after overnight incubation in DMEM with 5% FBS. After 2 hours of incubation with *C. trachomatis* cells were treated with different concentrations of PEG-2S and subjected to $pH_i$ and $Na^+_i$ measurement at different time points according to manufacturer's protocols. In all assessments calibration curves were performed prior to the experiments. Fluorescent inverted microscope (TE-2000s Nikon) was used to obtain images and mean intensity was quantified using NIS Elements imaging software (Nikon, Mississauga, Ont.) and mean intensity was quantified using NIS Elements imaging software (Nikon, Mississauga, Ont.).

Statistical Analysis

Data are presented as mean±SEM unless otherwise stated. Differences between treatment groups were assessed by one-way analysis of variance using the Student-Newman-Keuls method. A probability of P≤0.05 was considered statistically significant.

Chlamydial Invasion Perturbs Ion Homeostasis of Infected Cells.

Figure 18:
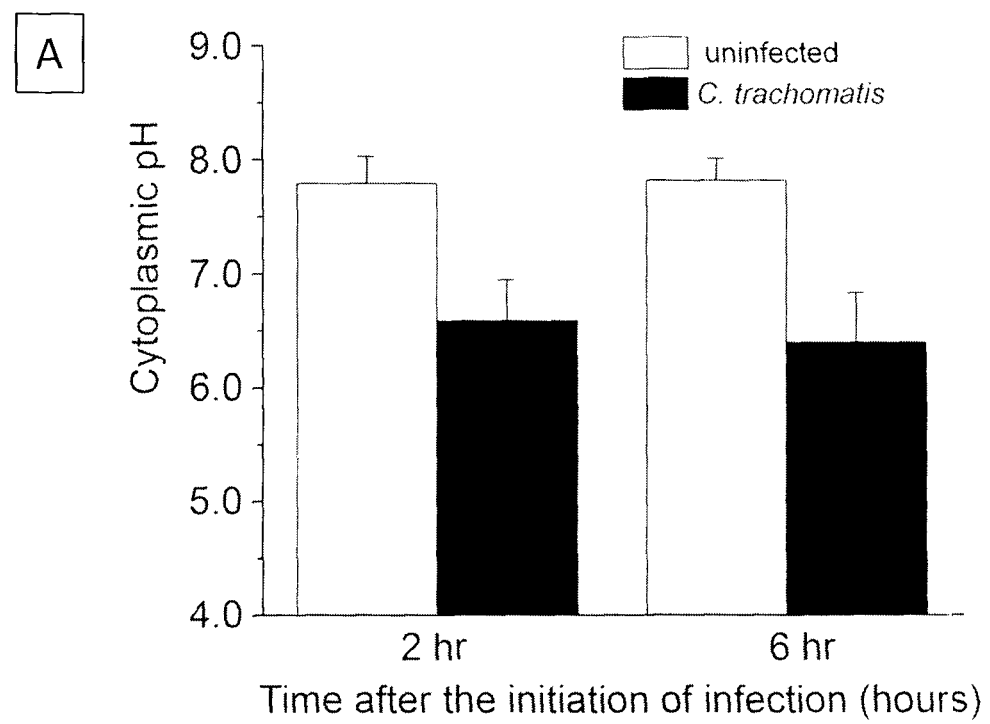
FIG. 18 shows changes in cytoplasmic pH (A) and $Na^+$ content (B) caused by the *C. trachomatis* infecting the HEK293 cell culture in high glucose medium.
Figure 18:
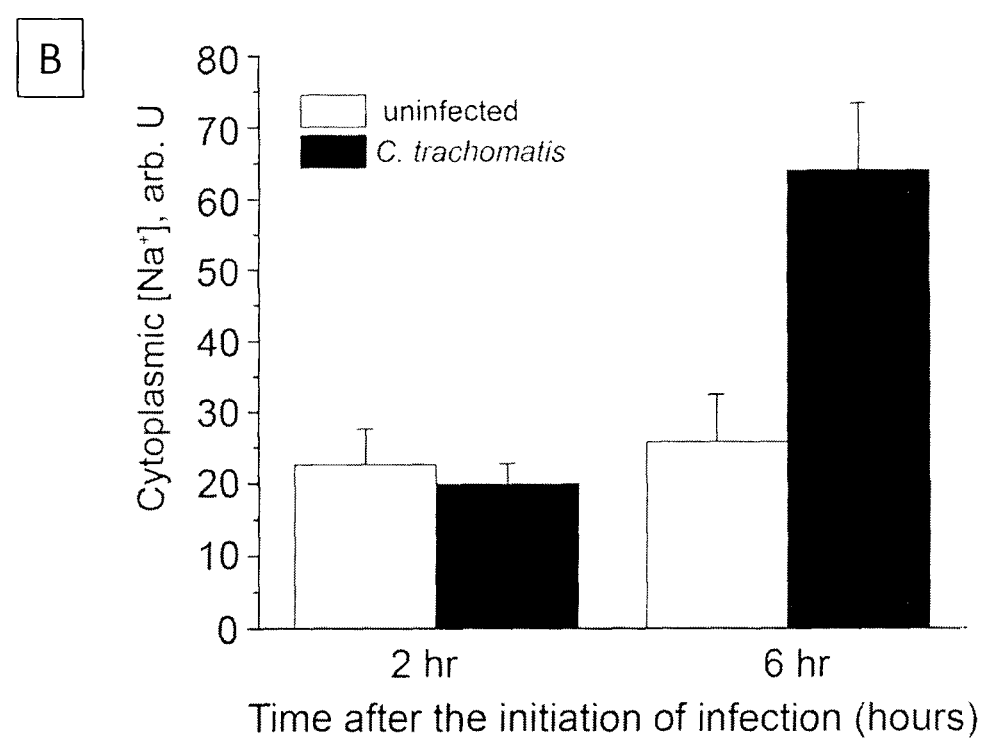

Changes in cytoplasmic pH and $Na^+$ content caused by the *C. trachomatis* infecting the HEK293 cell culture are shown in FIG. 18. Internal pH in uninfected control did not change in the course of observation (values of ~7.75 at 2 hr and at 6 hr time points were identical to the pH in uninfected cells of this lineage at zero time (not shown)), while in infected cells by 2 hrs of infection cytoplasmic pH dropped to ~6.6 and reached ~6.4 by 6 hrs (FIG. 18A). Significant acidification of the cytoplasm in cells infected by Chlamydiae was hypothesized because at the onset of the infection, this parasite rapidly consumes two preferable energy substrates, ATP and glucose.

It was further hypothesized that a relative acidification of the cytoplasm together with depletion of the host ATP pool caused by the metabolic activity of chlamydial reticulate bodies (RBs) would (i) slow down the $Na^+$ export by $Na^+/K^+$ ATPase and (ii) stimulate $Na^+$ uptake via $Na^+/H^+$ antiporter(s) residing in the host cell membrane, thus resulting in a rise of intracellular sodium. Parallel measurements of internal $Na^+$ in uninfected and infected HEK293 cells presented in FIG. 18B, indeed show a gradual increase of cytoplasmic $Na^+$ in *chlamydia*-infected cells (black bars) but not in the control uninfected cells (empty bars) delayed relative to the observed acidification.

Inhibitor of Chlamydial $Na^+$-NQR, Korormicin, Suppresses Proliferation of RBs but it is Toxic to Mammalian Cells.

Like other members of the *Chlamydia* genus, *C. trachomatis* encodes $Na^+$-dependent symporters for the accumulation of a number of important substrates, including amino acids and dicarboxylates. Therefore, maintenance of the transmembrane sodium gradient becomes a prerequisite for the proliferation of *C. trachomatis*. Since $Na^+$-NQR is the major primary $Na^+$ pump in this bacterium, its inhibition might have a strong anti-chlamydial effect. Korormicin, an antibiotic initially isolated from a marine bacterium, *Pseudoalteromonas* sp., is known to be an $Na^+$-NQR inhibitor and a bactericidal agent that is effective against marine bacteria but not against terrestrial microorganisms (Yoshikawa et al. Korormicin, a novel antibiotic specifically active against marine gram-negative bacteria, produced by a marine bacterium. J Antibiot. 1997; 50:949-953). Attractive features of korormicin are (i) its high efficiency ($K_i \approx 8 \times 10^{-11}$ M in preparations of isolated enzyme) and (ii) specificity, as it apparently has no effect on $Na^+$-independent NADH oxidoreductases.

Figure 5:
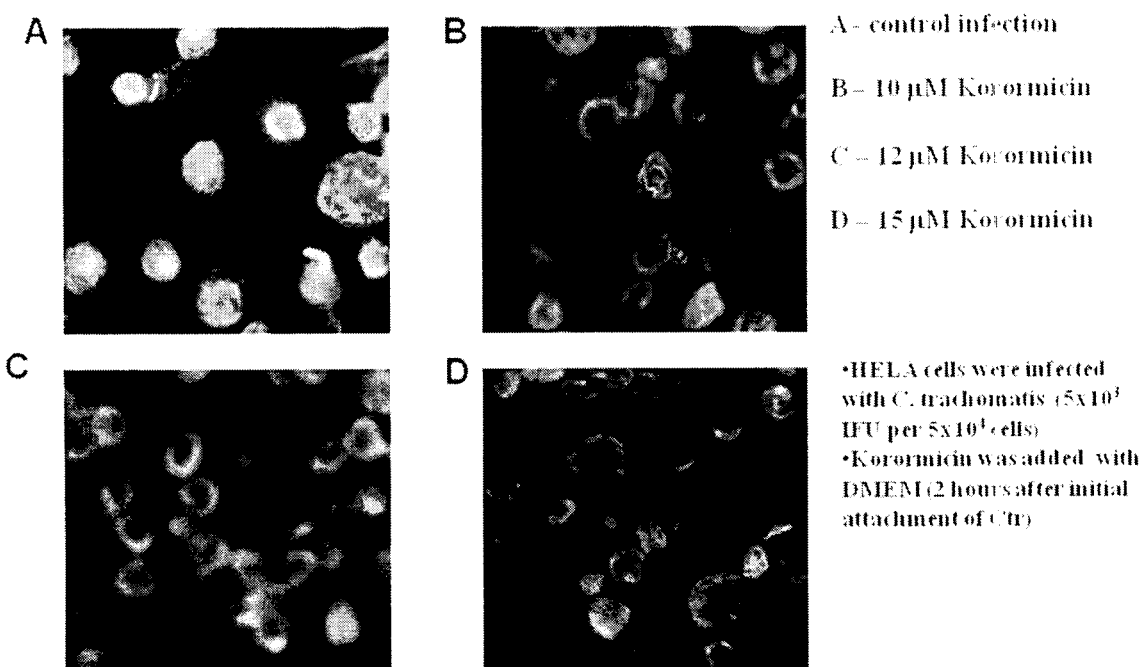
FIG. 5 shows an effect of korormicin on *C. trachomatis* infection of HeLa cells.
Figure 6:
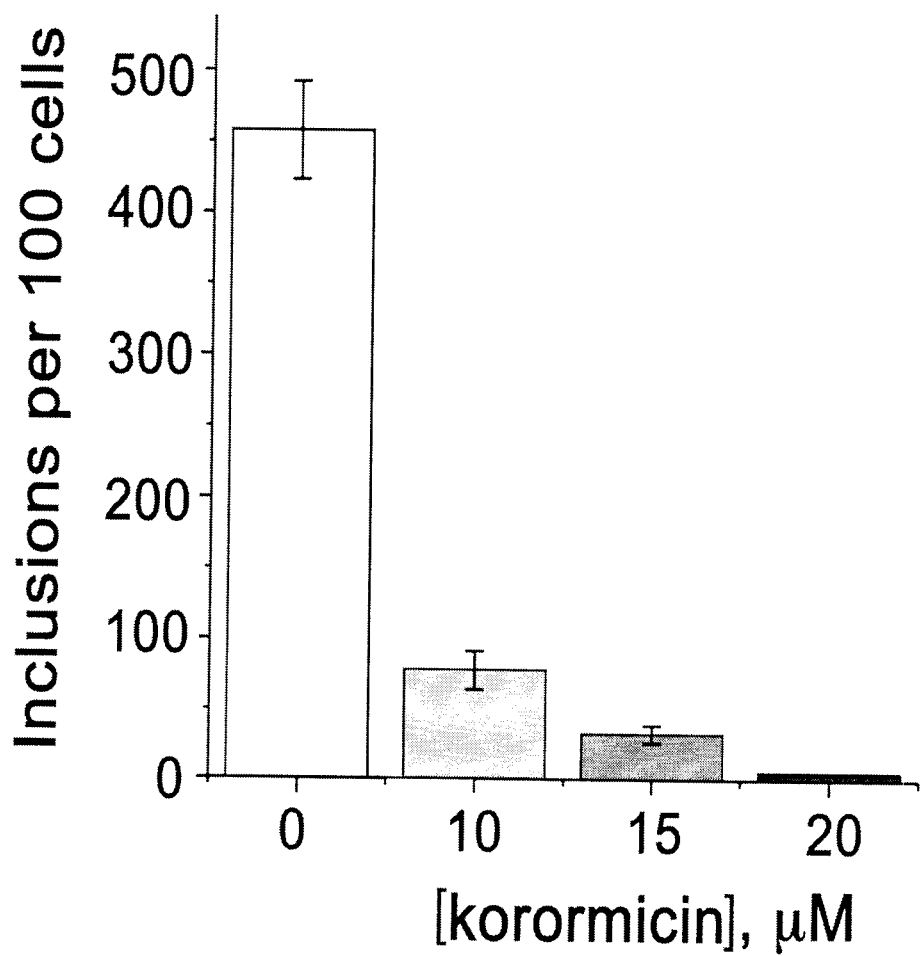
FIG. 6 shows a decline of intruding *C. trachomatis* after 5 consecutive treatments with korormicin.

Korormicin was evaluated in the first set of experimental examples above for potential antibiotic targeting chlamydial $Na^+$-NQR by examining its effects on the growth of the *C. trachomatis* in cell culture models. It has been found that korormicin is effective against *C. trachomatis* when added at a concentration of 10 to 20 µM (FIGS. 5 and 6). Fluorescent microscopy images clearly indicated decrease in number of viable *C. trachomatis* cells in cell cultures treated with korormicin (FIG. 5). Sharp decline of infectivity after five consecutive treatments with korormicin was evident already at 10 μM of added antibiotic; at 20 μM, number of chlamydial inclusions was less than 2% of control (FIG. 6). Calculated $MIC_{50}$ for korormicin (after $1^{st}$ treatment) was close to 3.00 mM. This concentration exceeds the effective inhibitory concentration measured for isolated $Na^+$-NQR by approximately six orders of magnitude. Such a significant discrepancy does not seem altogether surprising given an essential hydrophobicity of korormicin molecule (FIG. 4) and a number of membrane barriers, which potentially can scavenge korormicin before it gets to its target in situ. One could also argue that the antibiotic could be metabolized to some extent by mammalian and/or chlamydial cells.

Unfortunately, korormicin also had a palpable cytotoxic effect on mammalian cells (FIG. 7). Proliferation of the primary culture of vascular smooth muscle cells (VSMC) was used as a sensitive experimental model of cell response to a potentially toxic insult. As shown in FIG. 7, cells were sensitive even to nanomolar concentrations of added antibiotic; korormicin at concentrations of 5 to 15 μM lowered the cell titer by ~10%. Thus, although the experiments with korormicin confirmed the crucial role of $Na^+$-NQR in the metabolism and, therefore, proliferation and infectivity of *C. trachomatis*, this inhibitor cannot be used as anti-chlamydial remedy due to its toxic effect and low efficiency in the cell culture model of infection, which could be regarded as a reasonable $1^{st}$ approximation of infected tissue.

Design of Synthetic $Na^+$-NQR Inhibitor, PEG-2.

Korormicin and another $Na^+$-NQR inhibitor, HQNO, bind to the integral membrane subunit NqrB of the $Na^+$-NQR complex, which harbors the transmembrae $Na^+$ translocation pathway. HQNO and korormicin are mutually exclusive inhibitors, and their binding sites on NqrB are presumably overlapping although not identical. The chemical structure of koromicin is shown in FIG. 4. The four isolated chiral centers in korormicin molecule allows eight possible stereoisomers, but only one of them, the (5S,3'R,9'S,10'R) isomer (shown in FIG. 4) is the natural antibiotic.

Mode of action of both HQNO and korormicin indicates that the quinone-like "heads" may be the active structural modules responsible for binding the NqrB and that the geometry of polar groups may determine potency of a given inhibitor. Both structures also have a prolonged aliphatic "tail", which could be important for both crossing membrane barriers and docking of inhibitors to its target (they could be binding NqrB from within the lipid bilayer). In koromicin, the conjugated diene (4'C-7'C), followed by the epoxy group at 9'C-10'C could play a role of a rigid "spacer" separating the biologically active "head" of korormicin from a chaotic "tail". The epoxy group at 9'C-10'C was identified as a possible source of korormicin toxicity. It is known to react with amino-, hydroxyl and carboxyl groups as well as inorganic acids. Delayed and immediate epoxy dermatitis has been reported. Certain epoxy compounds have mutagenic potential (i.e., they are potentially carcinogenic).

Taking all these structural considerations into account, design of a non-toxic $Na^+$-NQR inhibitor took the following approach: (i) To eliminate the cytotoxic effect of natural korormicin, its epoxy group, as a possible source of toxicity, was removed from the structure. (ii) Further, the aliphatic "tail" of korormicin was shortened to 7 carbon atoms to potentially lessen the overall hydrophobicity of the molecule and thus lower its effective anty-chlamydial concentration. This approach yielded a compound, PEG-2 (FIG. 4), which has been shown to be a potent $Na^+$-NQR inhibitor and can be used as a structural platform for the further development of $Na^+$-NQR inhibitors.

Pharmacological Properties of PEG-2.

Due to the presence of two chiral centers in the molecule, four stereoisomeres of PEG-2 are possible (see FIG. 4). Preparations of PEG-2 obtained in the course of non-stereospecific synthesis carried out by Enamine Ltd (Kiev, Ukraine) were used in the first set of experimental examples described above. According to the manufacturer's report, this enantiomeric mixture contained no more than 10% of the presumably active isomer shown in FIG. 4.

Figure 10:
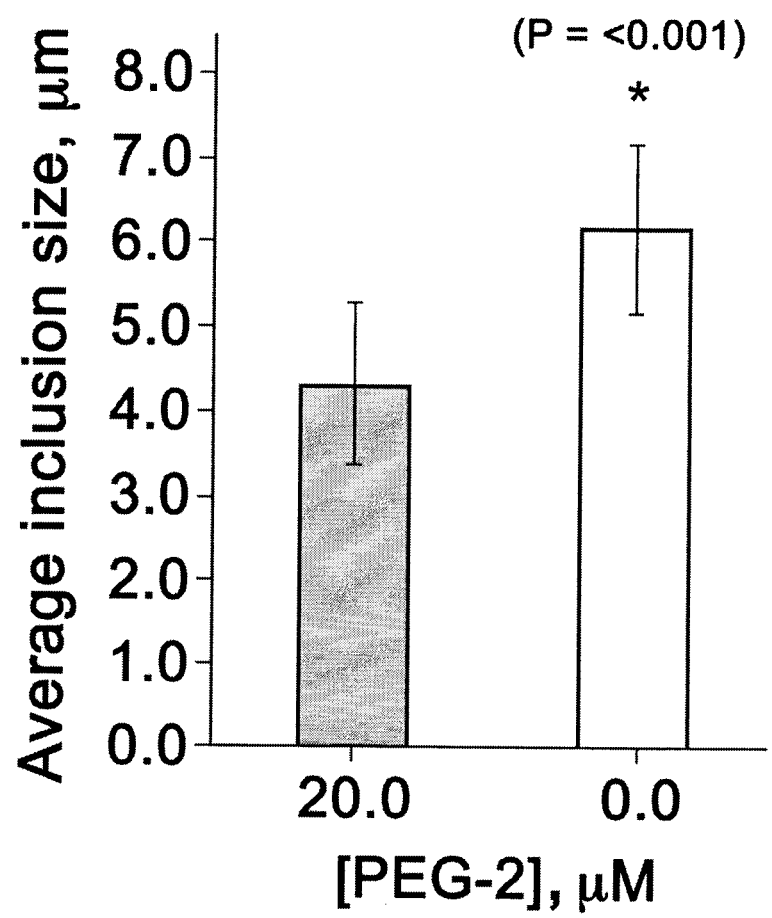
FIG. 10 shows a quantification of the effect shown in FIG. 9.
Figure 11:
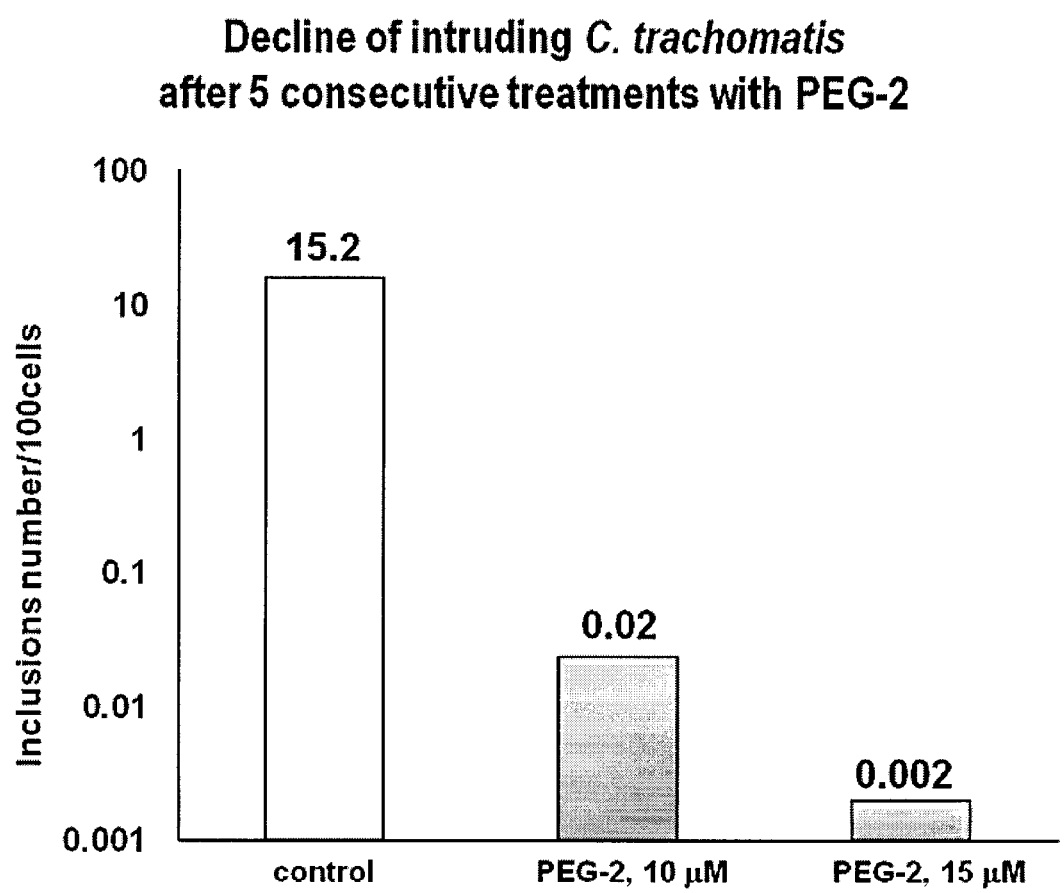
FIG. 11 shows a decline of intruding *C. trachomatis* after 5 consecutive treatments with PEG-2.
Figure 12:
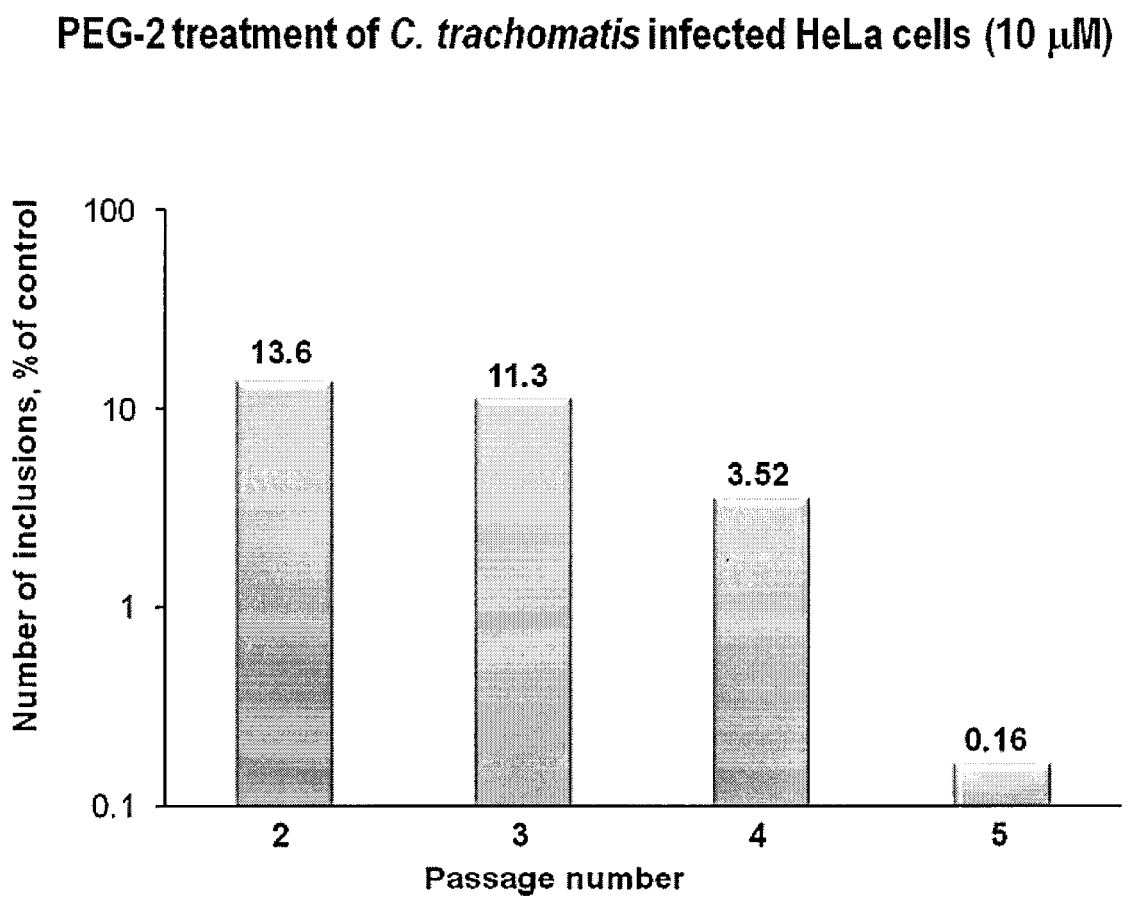
FIG. 12 shows a PEG-2 treatment (10 μM) of *C. trachomatis* infected HeLa cells as a function of passage number.
Figure 13:
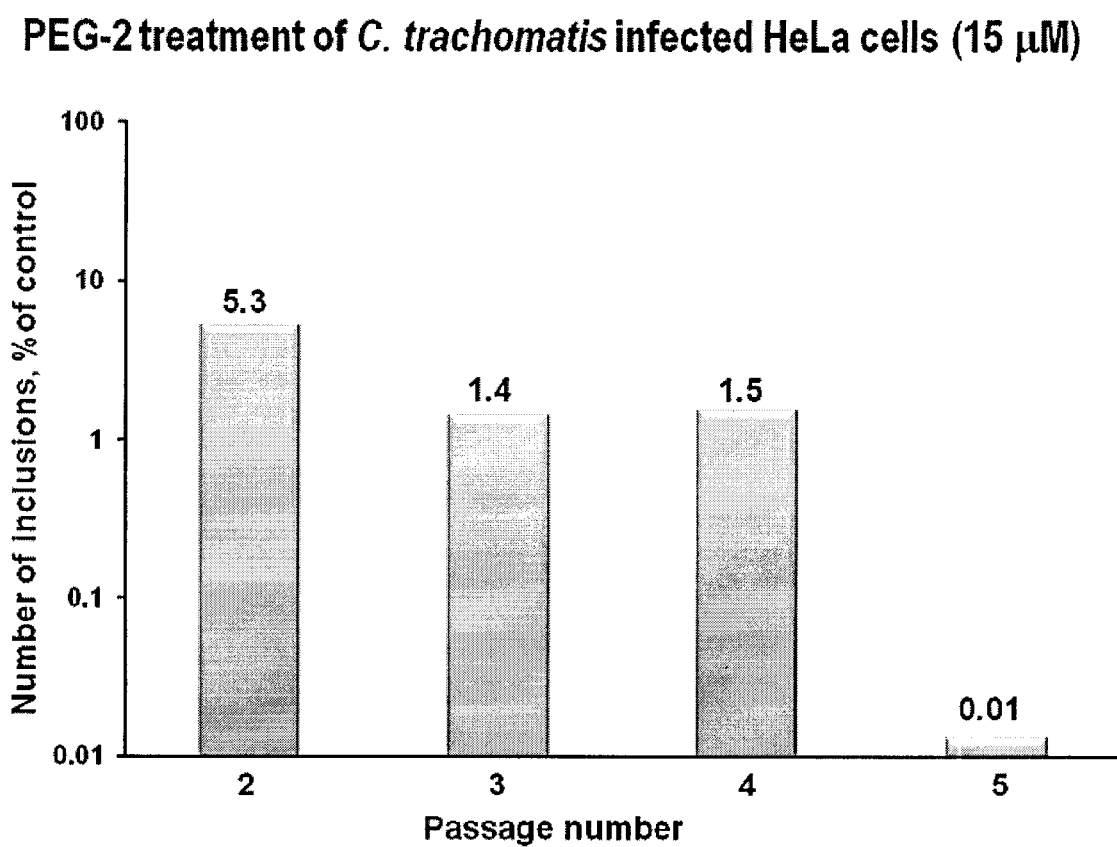
FIG. 13 shows a PEG-2 treatment (15 μM) of *C. trachomatis* infected HeLa cells as a function of passage number.
Figure 14:
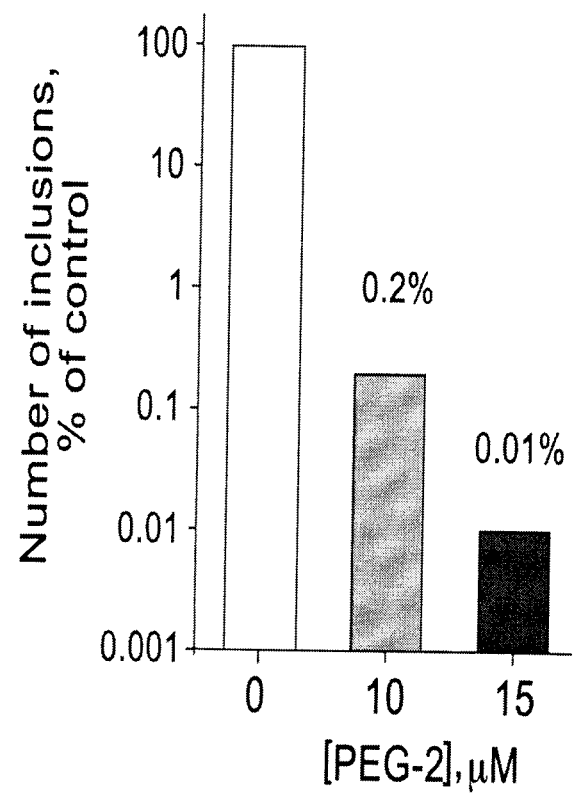
FIG. 14 shows a comparison of efficacy of PEG-2 versus korormicin in HeLa cells infected with *C. trachomatis*.
Figure 14:
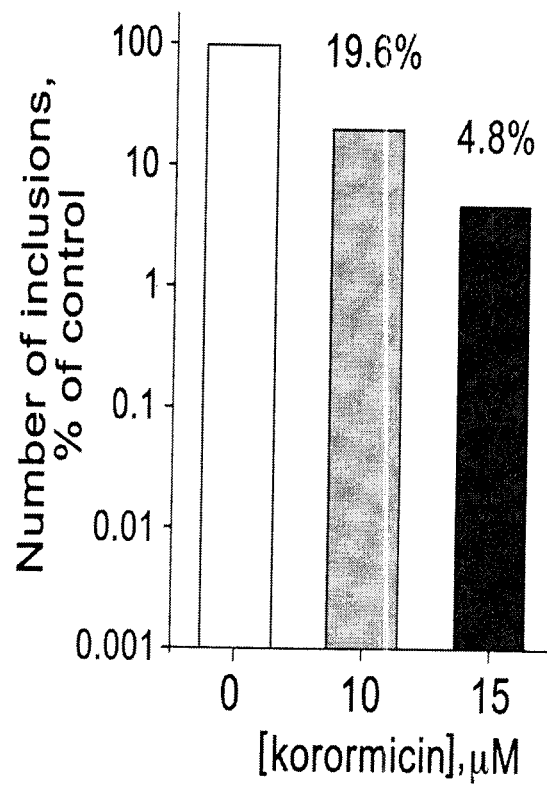
Figure 15:
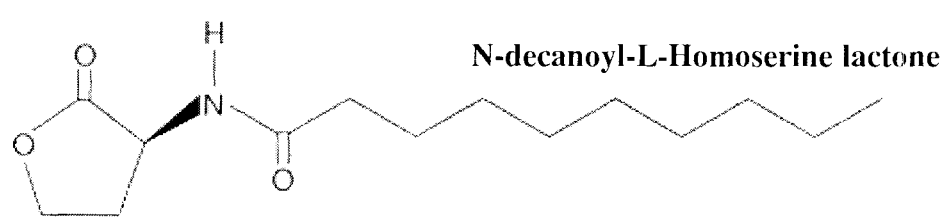
FIG. 15 shows chemical structures of homoserine lactones tested for HeLa cell toxicity and anti-chlamydial efficacy.
Figure 15:
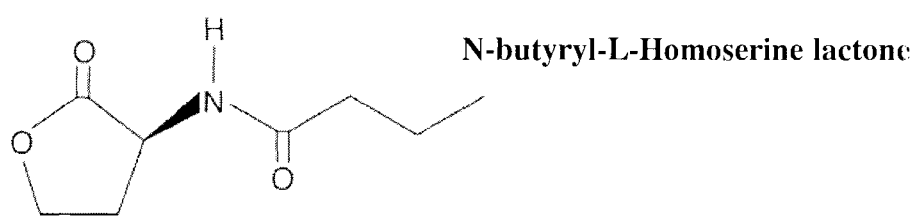
Figure 15:
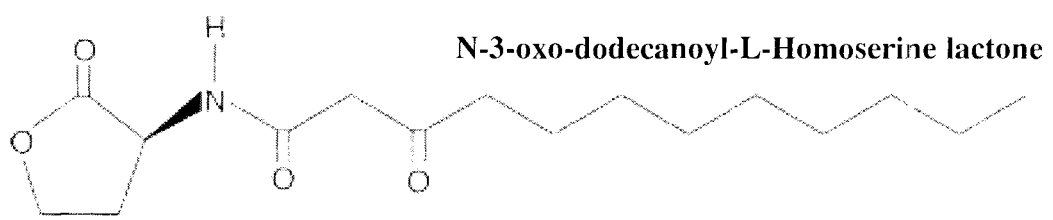
Figure 15:
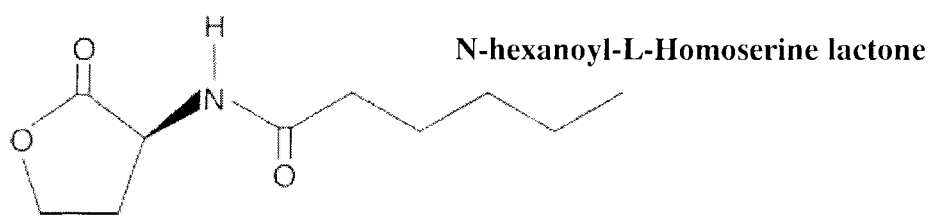
Figure 16:
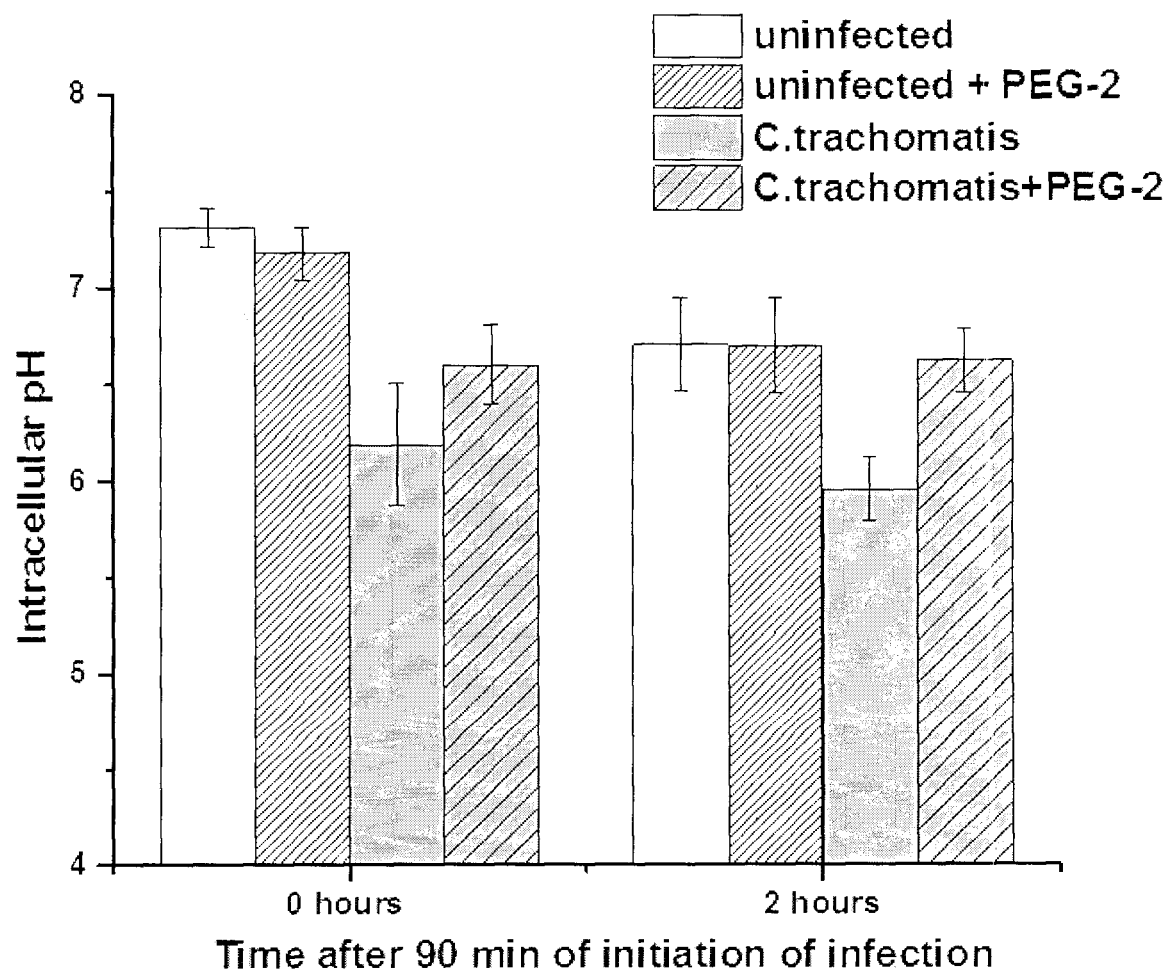
FIG. 16 shows an effect of PEG-2 on initial *C. trachomatis*-induced acidification of the cell cytoplasm.
Figure 17:
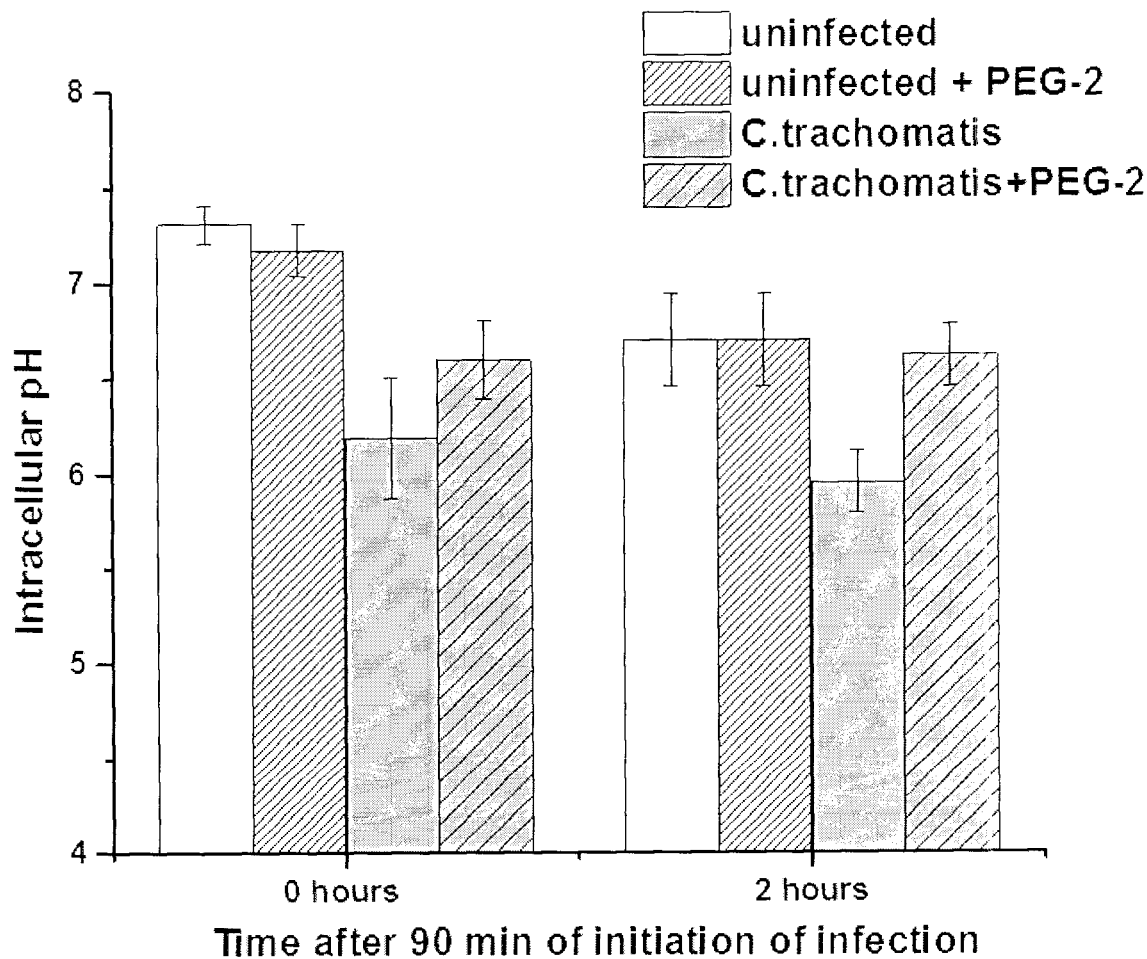
FIG. 17 shows an effect of PEG-2 on *C. trachomatis*-induced acidification of the cell cytoplasm at various time-points after infection (0, 2 hours, and 24 hours).
Figure 19:
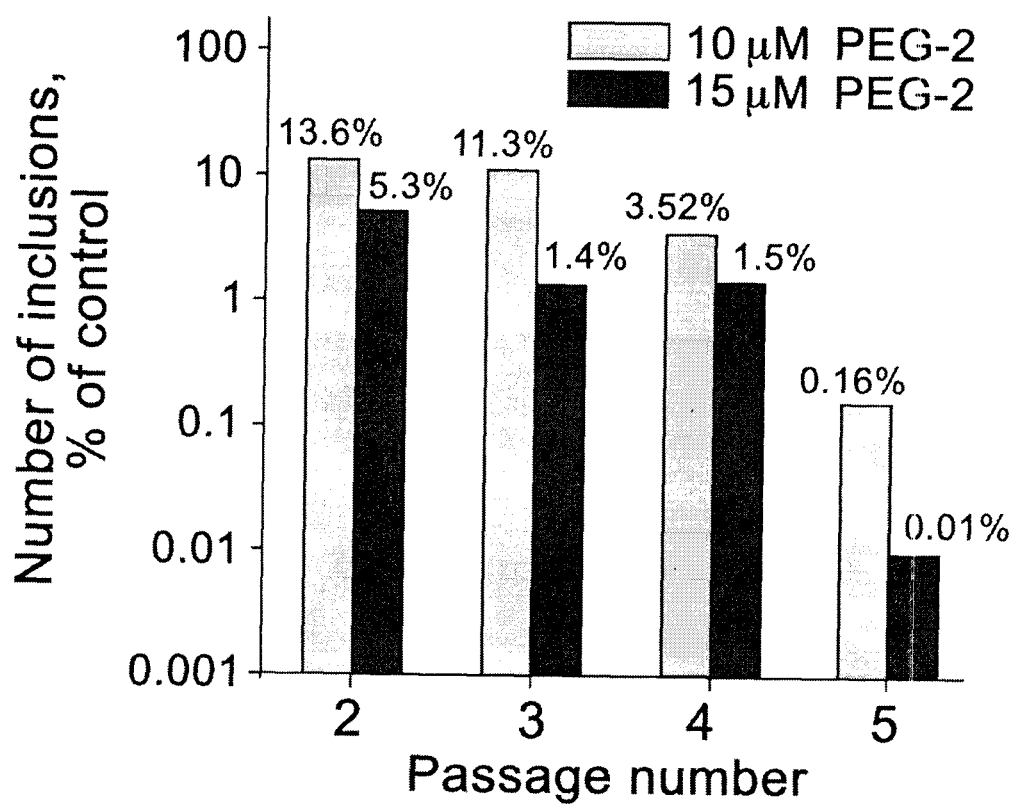
FIG. 19 shows that PEG-2 acts in a dose-dependent manner to reduce inclusion numbers during chlamydial infection, with inclusion numbers counted after $2^{nd}$, $3^{rd}$, $4^{th}$, and $5^{th}$ consecutive treatments.

Fluorescent microscopy confirmed that already a single treatment with PEG-2 had drastic effect on infection of HeLa cells by *C. trachomatis* (FIG. 9). Chlamydial inclusions formed in the presence of PEG-2 were hollow (FIG. 9, right image) compared to the control non-treated cell culture (FIG. 9, left image). They were also noticeably smaller (FIG. 10). Thus PEG-2 retained anti-chlamydial activity. Direct comparison to korormicin showed that enantiomeric mixture of PEG-2 is considerably more effective (FIG. 14): after 5 consecutive treatments with 15 µM PEG-2, number of inclusions was 0.01% of control, while at the same concentration of natural korormicin it was 4.8%. Therefore, in this model of infection, anti-chlamydial effect of a given batch of PEG-2 exceeded that of korormicin by at least 2 orders of magnitude. PEG-2 acts in a dosage-dependent manner. As FIG. 19 shows, while the $1^{st}$ treatment with 15 µM enantiomeric mixture of PEG-2 resulted in ~5-fold decrease of infectivity (measured as the number of chlamydial inclusions in the next passage), after 5 consecutive treatments the number of detectable inclusions was 10,000 times lower. PEG-2S was even more effective as anti-chlamydial agent than PEG-2 (Table 3): MIC50 for PEG-2S was 0.7 µM and MIC50 for PEG-2 was 10 µM. This trend continued after two consecutive treatments: $MIC50_2$ for PEG-2S was 0.25 µM versus 4 µM for PEG-2 (Table 3).

TABLE 3

Chlamydicidal properties of natural antibiotic Korormicin and synthetic $Na^+$-NQR inhibitor PEG-2.

| | Korormicin | PEG-2[a] | PEG-2S[e] |
|---|---|---|---|
| $MIC50_1$[b] | 18 µM (8.28 µg/ml) | 10 µM (3.63 µg/ml) | 0.7 µM (0.25 µg/ml) |
| $MIC50_2$[c] | 10 µM (4.6 µg/ml) | 4 µM (1.45 µg/ml) | 0.25 µM (0.09 µg/ml) |
| MCC2[d] | ND | 15 µM (5.45 µg/ml) | 1.0 µM (0.36 µg/ml) |

Figure 7:
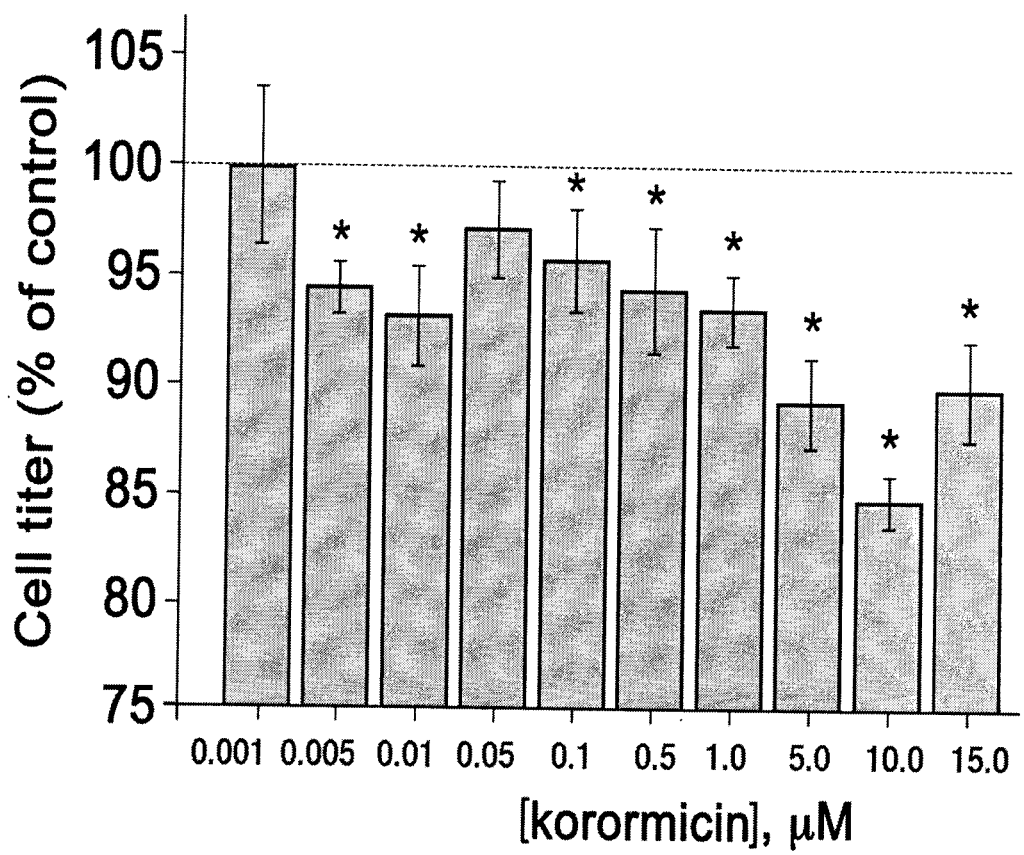
FIG. 7 shows a toxic effect of korormicin for primary Vascular Smooth Muscle cells.
Figure 8:
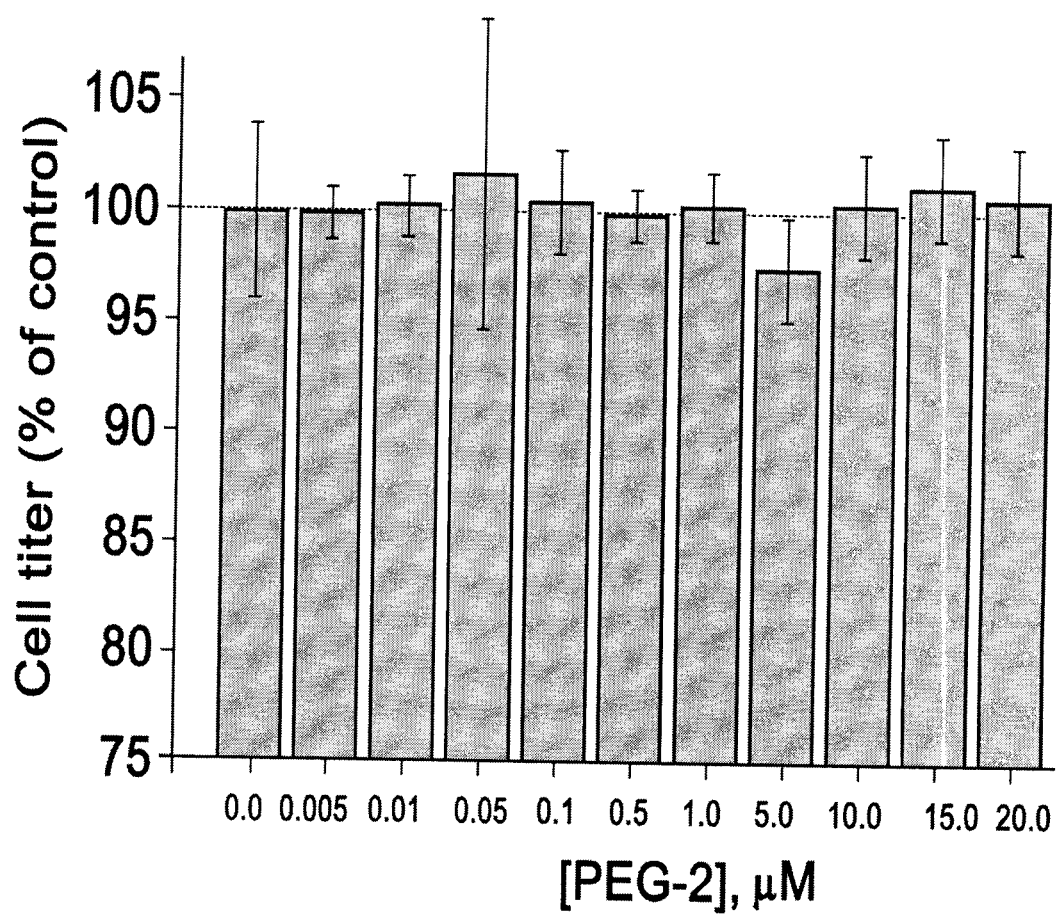
FIG. 8 shows an absence of toxic effect of PEG-2 for primary Vascular Smooth Muscle cells.

[a]Enantiomeric mixture, PEG-2, contained no more than 10% of the biologically active stereoisomer PEG-2S (according to the manufacturer's report);
[b]Minimal Inhibitory Concentration after the treatment;
[c]Minimal Inhibitory Concentration after the second treatment;
[d]Minimal Chlamydicidal Concentration of added antibiotic;
[e]Pure stereoisomer PEG-2 is Non-Toxic and Highly Selective Antibacterial Agent PEG-2 as well as PEG-2S provide a benefit of low cytotoxicity to mammalian cells: in contrast to natural korormicin, no toxic effects of PEG-2 on primary cell cultures (VSMC) were detected up to 20 µM of added PEG-2 (FIG. 8; compare to FIG. 7). Thus the koromicin epoxide at 9'C-10'C (see FIG. 4) apparently is the major reason for the cytotoxicity of korormicin.

One of the most appealing features of natural korormicin is its high selectivity as an inhibitor. It exclusively inhibits $Na^+$-NQR, and this enzyme has no homologues in mammalian cells as well as in the majority of benign bacterial microflora and free-living species. In this respect, narrowly targeted or selective inhibitors of $Na^+$-NQR would be "clean antibiotics" with no unwanted side effects and minimized potential to provoke an uncontrolled spread of drug resistance via mutant selection in multiple environmental species and following lateral gene transfer, as presently occurs with conventional antibiotics.

Figure 20:
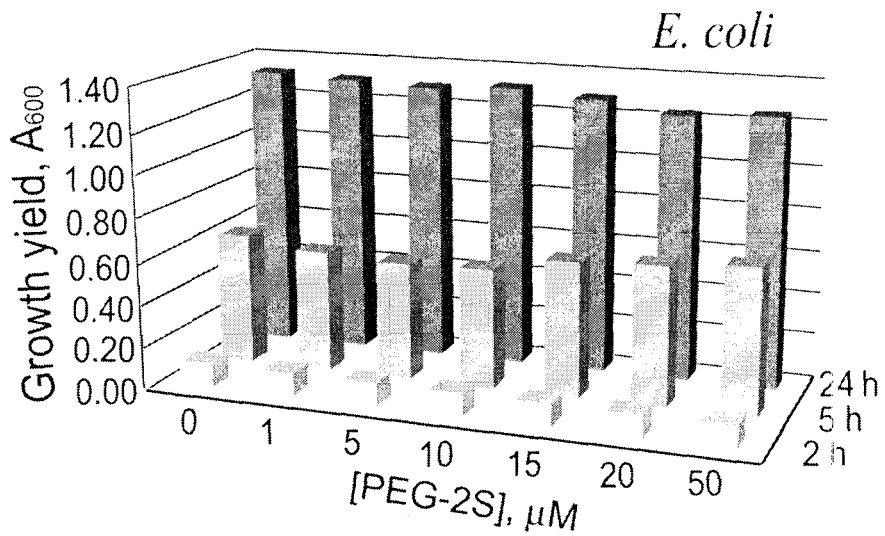
FIG. 20 shows that PEG-2S is highly selective anti-$Na^+$-NQR agent in that growth yield of three $Na^+$-NQR-negative species belonging to benign gut microflora in liquid medium was not effected at any tested concentration of added PEG-2S.
Figure 20:
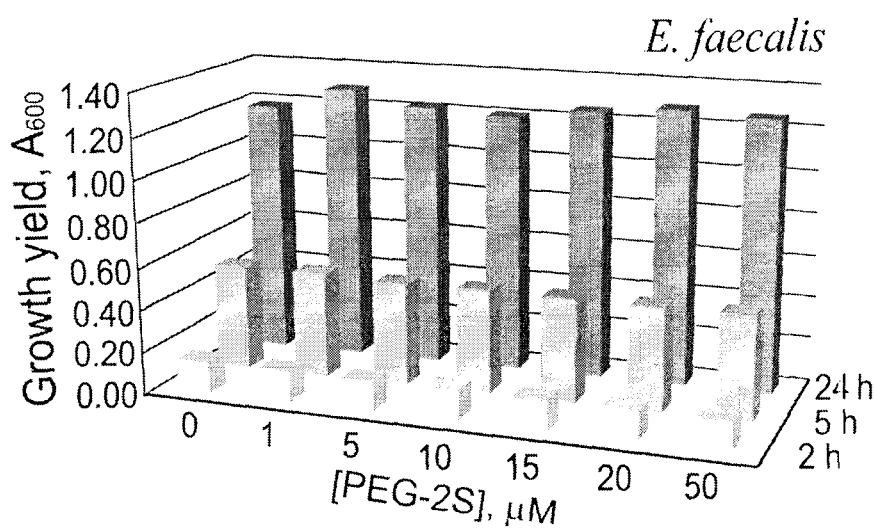
Figure 20:
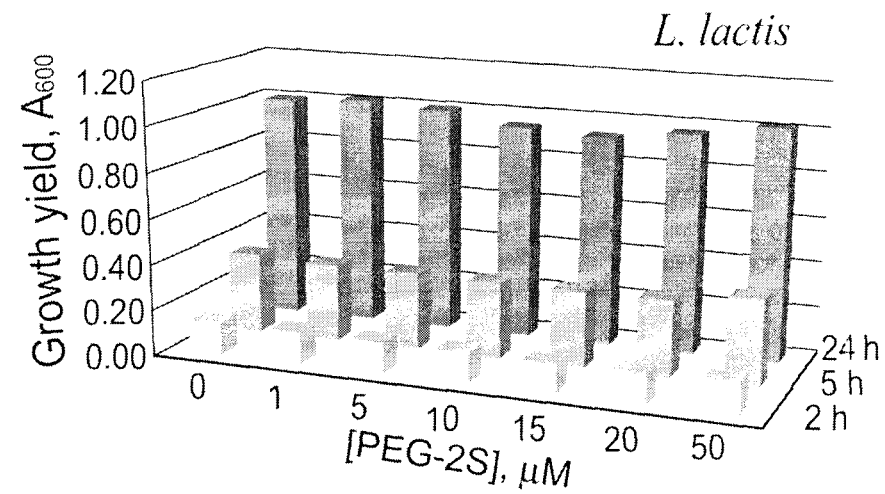

As FIG. 20 shows, PEG-2S added at 1.0 to 50 µM concentrations did not affect the growth of $Na^+$-NQR-negative representatives of the benign gastrointestinal microflora, *Escherichia coli* (upper panel), *Enterococcus faecalis* (middle panel), and *Lactococcus lactis* (lower panel). Susceptibility tests of the growth of pathogenic *Clostridium difficile* to PEG-2S by a standard paper disc method, which is routinely used to test antimicrobial action of korormicin, yielded the same result: PEG-2S does not affect the growth of *C. difficile* ATCC 700057 at the concentrations tested (0.5 µM-50 µM) (data not shown). Of note, gram-positive *C. difficile* possesses the ancestral form of $Na^+$-NQR, RNF. The Gly140 residue conserved in NqrB subunits of all known $Na^+$-NQR enzymes and implicated in binding of korormicin, is absent in a homologous subunit of RNF. One can therefore conclude that PEG-2 and PEG-2S upheld the high selectivity of inhibitory action that is characteristic for korormicin.

Direct Measurements of Inhibition of $Na^+$-NQR by PEG-2S.

Activity of $Na^+$-NQR could be measured in a number of experimental setups. In the context of this work, an especially attractive model is the registration of the $Na^+$-NQR-mediated oxidation of NADH in sub-bacterial membrane vesicles. This approach can monitor $Na^+$-NQR activity directly in real time and can test $Na^+$-NQR inhibitors with the enzyme operating in a physiologically relevant background (being placed in its native membrane and feeding the electrons taken from NADH to the respiratory chain) but without additional permeability barriers and influences from cytoplasmic metabolism.

$Na^+$-NQR from the dangerous human pathogen *Vibrio cholerae* is the most extensively studied representative of the class. This enzyme was therefore chosen to test inhibitory properties of PEG-2. For these experiments in sub-bacterial vesicles, purified active stereoisomer of PEG-2, PEG-2S (structure shown in FIG. 4), produced by stereospecific synthesis by Canam Bioresearch Inc (Winnipeg, Canada), was used.

Figure 21:
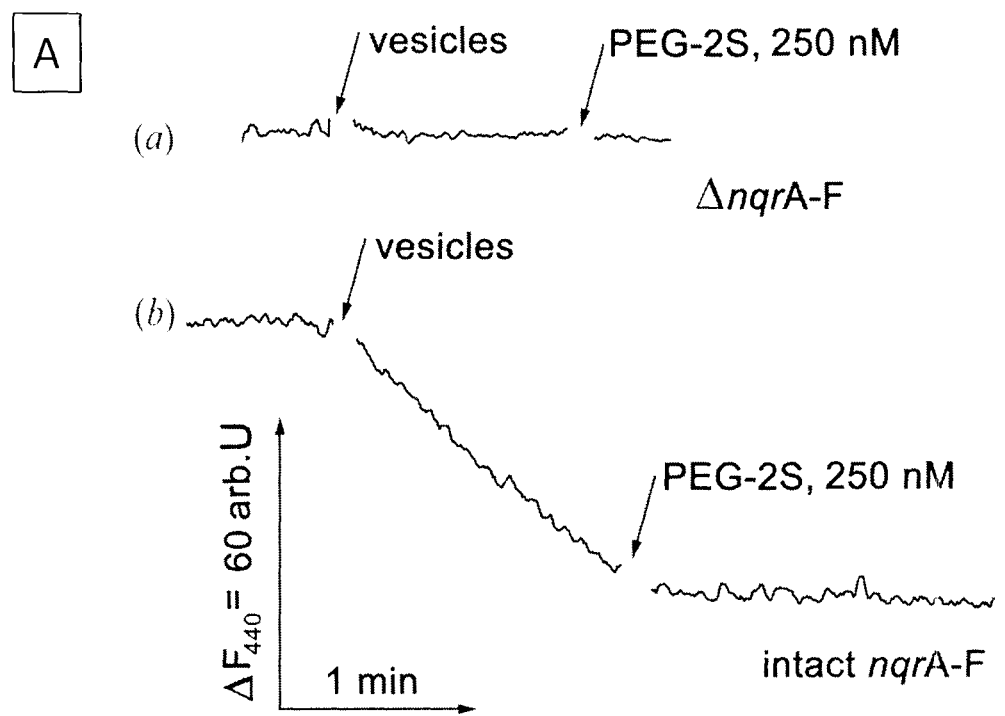
FIG. 21 shows inhibition of $Na^+$-NQR by PEG-2S as measured directly in sub-bacterial *V. cholerae* vesicles: (A) PEG-2S-sensitive oxidation of dNADH is absent in $Na^+$-NQR-deficient membranes (trace (a)), while $Na^+$-NQR-containing membranes oxidize dNADH in the PEG-2S-sensitive manner (trace (b); and (B) normalized $Na^+$-NQR activity (100% corresponds to the activity in the absence of the inhibitor) plotted as a function of [PEG-2S] for calculation of the $IC_{50}$ of PEG-2S inhibition.
Figure 21:
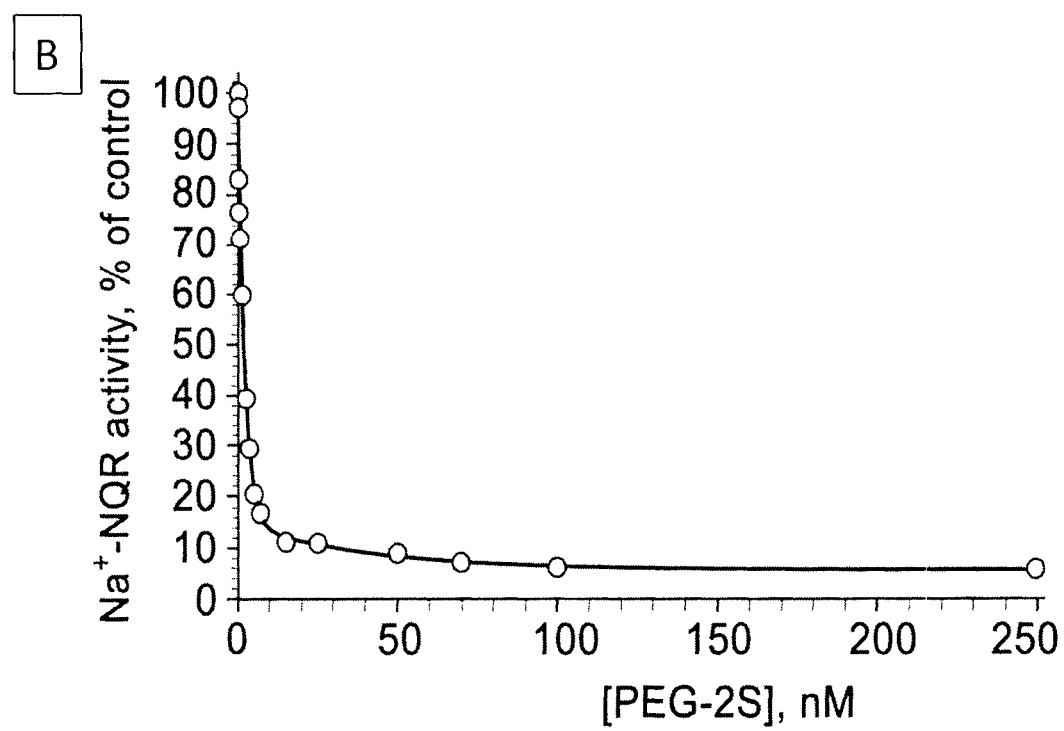

In addition to $Na^+$-NQR, membrane of *V. cholerae* contains another NADH-oxidizing enzyme, non-coupled NDH-2 (non-coupled NADH:ubiquinone oxidoreductase of type 2). While $Na^+$-NQR oxidizes both NADH and its analog dNADH with similar rates, NDH-2 cannot use dNADH as a substrate. Therefore, the dNADH-oxidase activity of membrane vesicles could be used to monitor $Na^+$-NQR selectively. Indeed, elimination of functional $Na^+$-NQR by the chromosomal nqr A-F deletion results in the inability of membrane vesicles isolated from the mutant *V. cholerae* strain to oxidize dNADH (FIG. 21A, trace (a)). In contrast, vesicles isolated from the isogenic $Na^+$-NQR-positive strain did oxidize dNADH in a PEG-2S-sensitive manner (FIG. 21A, trace (b)). Titration of the $Na^+$-NQR activity with PEG-2S in this experimental model yielded MIC$_{50}$ of 1.76 nM (FIG. 21B). For comparison, IC$_{50}$ for HQNO measured in the same experimental model was 130 nM.

PEG-2S Disrupts Chlamydial Infection in Cell Culture Model.

Figure 22:
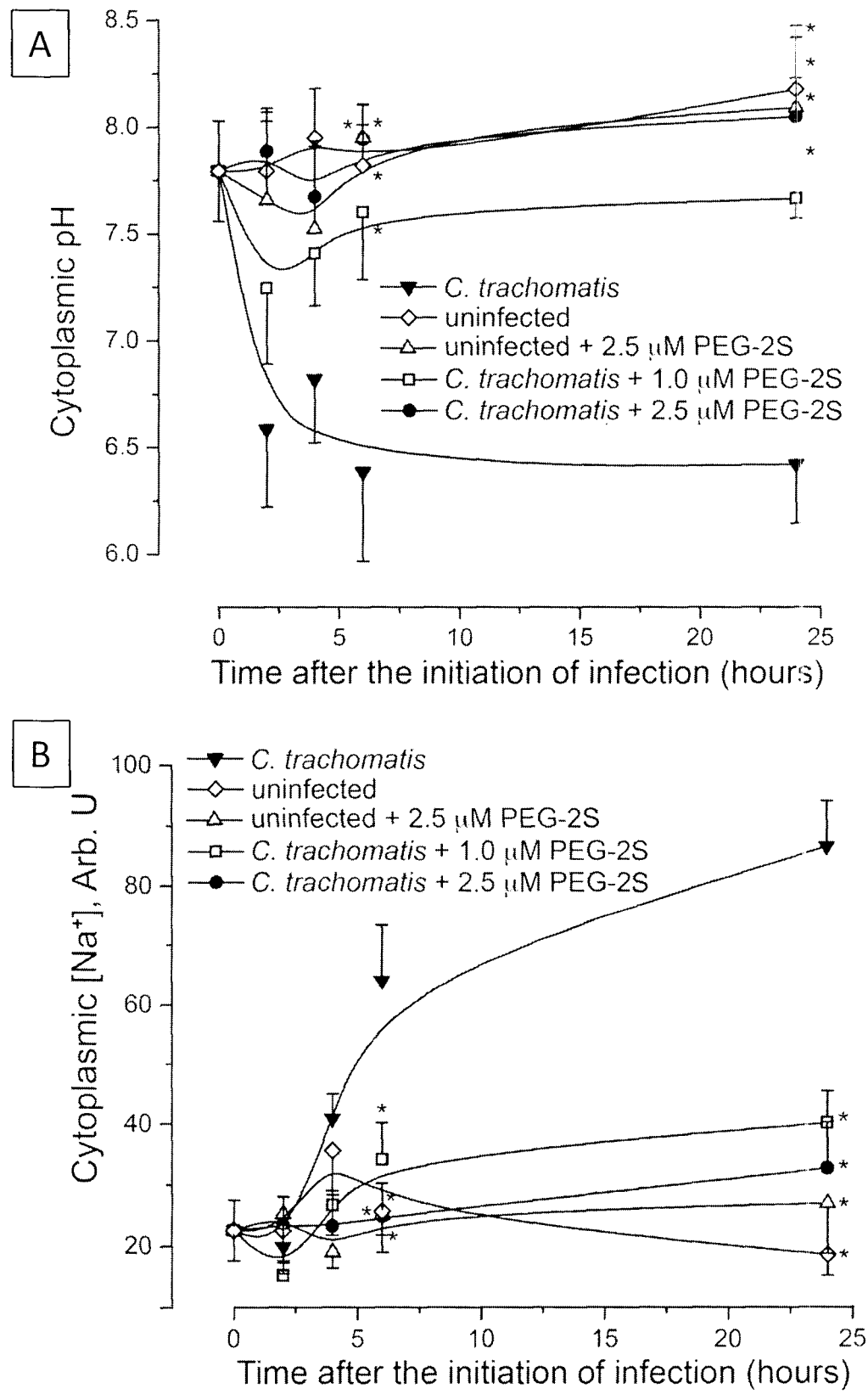
FIG. 22 shows that PEG-2S disrupts chlamydial infection in HEK293 cell culture.

Direct monitoring of cytoplasmic pH in HEK293 cells infected with *C. trachomatis* confirmed expectations (based on results shown in FIG. 18A) of rapid and deep acidification during the initial phase of chlamydial infection (FIG. 22A, black triangles). While the subtle transient changes of pH during first ~5 hrs of infection in uninfected cells (empty triangles) were not statistically significant, the addition of PEG-2S at 1.0 μM (empty squares) interrupted the *chlamydia*-caused acidification within first 5 hours of infection, resulting in almost complete relaxation of internal pH at ~7.6. At 2.5 μM, PEG-2S prevented the *chlamydia*-induced acidification completely (FIG. 22A, black circles). Of note, observed acidification of the cytoplasm in infected HEK293 cells persisted for a long (up to 24 hrs) time. This could be due to the high glucose content in the experimental medium used.

The initial acidification of the host cytoplasm should activate resident Na$^+$/H$^+$ exchange machinery, resulting in a rise of intracellular [Na$^+$]. As FIG. 22A shows, internal pH of infected cells indeed drops from homeostatic level of 7.75 to 6.5 after ~5 hr of infection (FIG. 22A, black triangles). Apparently, this alarming acidification activated NHE-type Na$^+$/H$^+$ exchanger(s) operating in the plasmalemma of HEK293 cells, as it is evident from the significant rise in cytoplasmic [Na$^+$] (FIG. 22B, black triangles). As expected based on results shown in FIG. 18, sodium accumulation was delayed relative to the acidification (compare FIGS. 18A and B; FIGS. 22A and B, black triangles). Again, the intracellular sodium accumulation was sensitive to the low μM concentrations of PEG-2S (FIG. 22B, empty squares and black circles).

Taken together, the data summarized in FIG. 18A,B and FIG. 22A,B support the idea about the manipulation of ion homeostasis of infected cell by invading *chlamydia* and demonstrate the importance of chlamydial Na$^+$-NQR for the infectious process.

These data support the use of PEG-2 and PEG-2S as an antibiotic and as a platform for the further design of drug derivatives for alternative antibiotics. Several illustrative prospective drug designs, including PEG-3 and PEG-4, are provided in FIG. 23 in alignment with PEG-2.

As is apparent from FIG. 23, both PEG-3 and PEG-4 have a "shielded" positive charge at the distal end of the aliphatic module of the molecule. It is expected that, compared to PEG-2, PEG-3 will be (a) more soluble and (b) able to accumulate in chlamydial cytoplasm against its concentration gradient. The guanidinum derivative, PEG-4 will share these beneficial features with PEG-3. In addition, it may potentially inhibit (very gently) the NHE-1 antiporter in the infected cells and thus lower intracellular [Na$^+$] and potentially function to further impede the development of chlamydial infection.

Further drug derivatives designed and synthesized from the PEG-2 platform and have been tested for solubility and antibiotic activity. Antibiotic activity is assessed using the *Chlamydia* infection of cell culture experimental model described above in both the first and second set of experimental examples. Fluorescence microscopy results shown in FIG. 24 indicate that treatment with each of the derivatives reduces inclusion size in *Chlamydia* infected cells.

Table 4 shows the summarized results of the testing with PEG-2S included to provide reference values. The derivatives PEG-6(Boc), PEG-10, PEG-11, PEG-14 all showed improved solubility compared to PEG-2S, with PEG-6(Boc) and PEG-10 providing particularly high solubility in DMSO. Antibiotic activity was also demonstrated for all of the derivatives shown in Table 4 with comparable IC50 values for anti-chlamydial efficacy.

TABLE 4

PEG series of antibiotics targeting chlamydial Na$^+$-NQR

| Name | Structure | IC$_{50}$(Chl), μM$^a$ | Solubility$^b$ |
|---|---|---|---|
| PEG-2S | 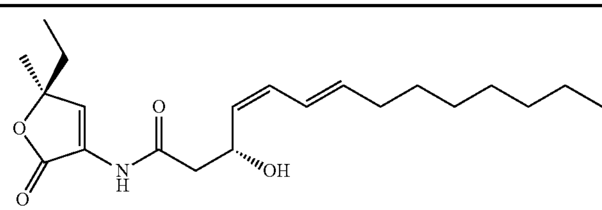 | 0.70 | +/− |
| PEG-6(Boc) | 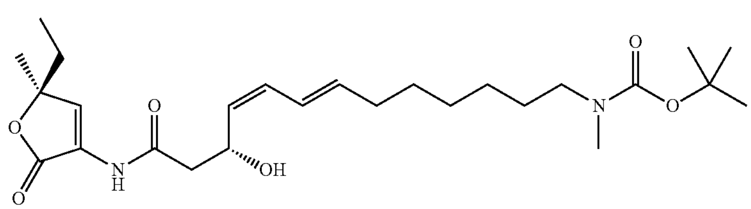 [SMILES: CC[C@@]1(C)C=C(NC(=O)C[C@@H](O)/C=C\C=C\CCCCCCN(C)C(=O)OC(C)(C)C)C(=O)O1] | 0.96 | +++ |
| PEG-10 | 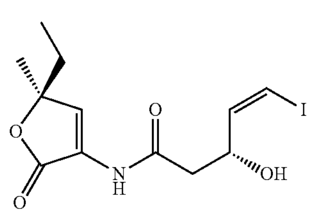 [SMILES: CC[C@@]1(C)C=C(NC(=O)C[C@@H](O)/C=C\I)C(=O)O1] | 0.67 | +++ |

TABLE 4-continued

PEG series of antibiotics targeting chlamydial Na⁺-NQR

| Name | Structure | IC$_{50}$(Chl), μM$^a$ | Solubility$^b$ |
|---|---|---|---|
| PEG-11 | 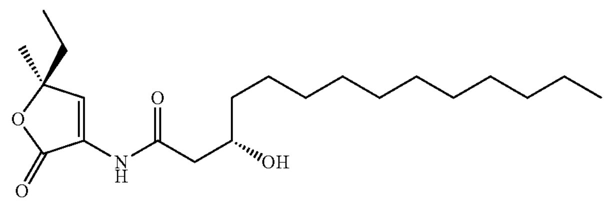 [SMILES: CCCCCCCCCCC[C@H](O)CC(=O)NC1=C[C@](C)(CC)OC1=O] | 0.63 | + |
| PEG-14 | 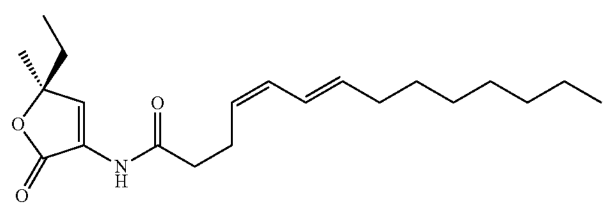 [SMILES: CCCCCCC/C=C/C=C\CCC(=O)NC1=C[C@](C)(CC)OC1=O] | 1.20 | + |

$^a$Concentration required for the half-maximal inhibition of the proliferation of *Chlamydia trachomatis* in cell culture experimental model.
$^b$Solubility in DMSO as assessed by a qualified observer. "+/−" insoluble at concentrations exceeding 25 mM; "+" solubilized at 50 mM completely after 20 min at room temperature; "++" solubilized at 50 mM after 5 min at room temperature; "+++" perfectly soluble in DMSO (instant solubilization at 50 mM)

The results provided herein support several novel findings. For example, the results support a novel method of antibacterial attack through Na⁺-NQR inhibition, and provide a novel demonstration of antibiotic treatment of bacterial infection of animal cells through Na⁺-NQR inhibition. It should be recognized that utility of PEG-2 and related compounds encompassed by formulae I, II, III or W are not to be limited by theory or mechanism regarding Na⁺-NQR inhibition.

Another example of a novel finding is that the previously discovered natural antibiotic korormicin can be improved by significantly reducing eukaryotic toxicity through removal of the epoxy group from its chemical structure with the creation of PEG-2. This marked reduction of drug toxicity through removal of an epoxy group is novel and not recognized by previous literature. Another example of a novel finding is that PEG-2 provides improved efficacy as an antichlamydial agent than koromicin. This increased efficacy is novel and unrecognized by previous literature. Another example of a novel finding, is that the supportive data demonstrates potential and reasonable prediction for further drug design modifications of PEG-2 leading to efficacious molecules to inhibit Na⁺-NQR in a wide variety of pathogenic bacteria.

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. An antibiotic compound of formula (III):

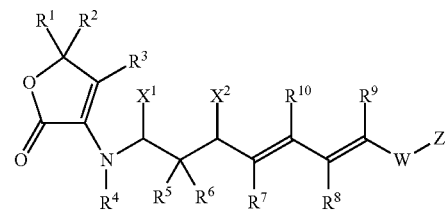

III or a salt or stereoisomer thereof;
wherein $R^1$-$R^3$ and $R^5$-$R^{10}$ are independently selected from the group consisting of H, alkyl group, halogen, OH, NH$_2$ and SH;
$R^4$ is H or alkyl group;
$X^1$-$X^2$ are independently selected from the group consisting of =O, =S, =NH, H, alkyl, halogen, OH, SH and NH$_2$;
W is a saturated acyclic hydrocarbon chain of 1 to 15 carbon atoms consisting only of hydrogen and carbon atoms; and
Z is CH$_3$.

2. The compound of claim 1, wherein the compound has only two chiral centers 5S and 3'R.

3. The compound of claim 1, wherein $R^4$ is H and $X^1$-$X^2$ are independently selected from =O or OH.

4. The compound of claim 1, wherein $R^1$-$R^{10}$ are independently selected from H or a C1-C3 alkyl group, $X^1$-$X^2$ are independently selected from the group consisting of =O, =S, H, halogen, OH and SH.

5. The compound of claim 4, wherein $R^4$ is H.

6. The compound of claim 1 selected from the group consisting of:

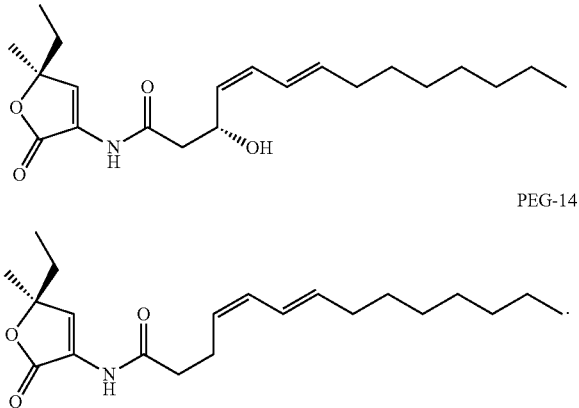

7. The compound of claim 6, wherein the compound has only two chiral centers 5S and 3'R.

8. A pharmaceutical composition comprising an antibiotic effective amount of the compound of claim 1 and a pharmaceutically acceptable carrier.

9. A pharmaceutical composition comprising an antibiotic effective amount of the compound of claim 6 and a pharmaceutically acceptable carrier.

10. A method of treating a bacterial disease comprising administering an effective amount of the compound of claim 1 to a subject in need thereof, wherein the bacterial disease is caused by a gram-negative bacteria.

11. The method of claim 10, wherein the bacterial disease is selected from the group consisting of cholera, acute gastroenteritis, ulcers, gastrointestinal infection, wound infection, septicemia, foodborne diarrhea, diarrhea, gastroenteritis, Legionnaires' disease, necrotizing gingivitis, adult periodontitis, periodontitis, juvenile periodontitis, meningitides, gonorrhea, pneumonia, endocarditis, otitis, chancroid, lung infections, skin infections, peritonitis, lesions, paratyphoid fever, typhoid fever, plague, Far East scarlet-like fever, bronchitis, trachoma, vaginitis, juvenile pneumonia, acute bronchiolitis, human fetal death, peritoneal infections, respiratory infection, middle ear infection, eye infection, and Central Nervous System infection.

12. The method of claim 10, wherein the bacterial disease is caused by an infection of a bacteria selected from the group consisting of *Vibrio cholera, Vibrio parahaemolyticus, Vibrio vulnificus, Vibrio gastroenteritis, Vibrio damsel, Vibrio fluvialis, Vibrio furnissii, Vibrio harveyi, Vibrio hollisae, Vibrio costicola, Vibrio mimicus, Vibrio cincinnatiensis, Aeromonas veronii, Aeromonas caviae, Legionella pneumophila, Treponema denticola, Porphyromonas gingivalis, Tannerella forsythia, Actinobacillus actinomycetemcomitans, Neisseria meningitides, Neisseria gonorrhoeae, Neisseria sicca, Haemophilus influenza, Haemophilus ducreyi, Pseudomonas aeruginosa, Pseudomonas pseudoalcaligenes, Photorhabdus asymbiotica, Salmonella enterica (S. Paratyphi), Salmonella enterica (S. Typhi), Klebsiella pneumonia, Yersinia pestis, Yersinia pseudotuberculosis, Chlamydophila pneumonia, Chlamydia trachomatis, Simkania negevensis Z, Waddlia chondrophila, Pasteurella multocida, Serratia proteamaculans, Bacteroides fragilis*, and *Moraxella catarrhalis*.

13. The method of claim 10, wherein the bacteria is a species from a proteobacteria order selected from the group consisting of Enterobacteriales, Vibrionalles, Pasteurellales, Aeromonadales, Pseudomonadales, and Neisserales.

14. The method of claim 10, wherein the bacteria is a Bacteroidetes.

15. The method of claim 10, wherein the bacteria is a Chlamydiae.

16. The method of claim 10, wherein the bacteria is selected from the group consisting of *Chlamydia trachomatis, Simkania negevensis Z, Candidatus Protochlamydia amoebophila* UWE25, *Chlamydia muridarum* Nigg', *Treponema denticola, Treponema putida, Porphyromonas gingivalis, Tannerella forsythia, Actinobacillus actinomycetemcomitans, Legionella pneumophila, Neisseria meningitides, Neisseria gonorrhoeae, Klebsiella pneumonia*, and *Chlamydophila pneumonia*.

17. The method of claim 10, wherein the compound is an antibiotic that is therapeutically effective in an amount that is non-toxic to mammalian cells.

18. The compound of claim 1, wherein
$R^1$-$R^3$ are independently selected from H or a C1-C3 alkyl group and $R^5$-$R^{10}$ are independently selected from H or a C1-C5 alkyl group;
$R^4$ is H; and
$X^1$-$X^2$ are independently selected from the group consisting of =O, =S, H, alkyl, halogen, OH and SH.

19. The compound of claim 18, wherein the compound has only two chiral centers 5S and 3'R.

20. The compound of claim 1, wherein
$R^1$-$R^3$ are independently selected from H or a C1-C3 alkyl group and $R^5$-$R^{10}$ are independently selected from H or $CH_3$;
$R^4$ is H;
$X^1$-$X^2$ are independently selected from =O, =S, H, OH, or SH; and
W is a saturated acyclic hydrocarbon chain of 1 to 8 carbon atoms consisting only of hydrogen and carbon atoms.

21. The compound of claim 20, wherein the compound has only two chiral centers 5S and 3'R.

* * * * *